US008609354B2

(12) United States Patent
Carpén et al.

(10) Patent No.: US 8,609,354 B2
(45) Date of Patent: Dec. 17, 2013

(54) METHOD FOR SELECTING PATIENTS FOR TREATMENT WITH AN EGFR INHIBITOR

(75) Inventors: Olli Carpén, Espoo (FI); Minnamaija Lintunen, Turku (FI); Raija Ristamäki, Turku (FI); Jari Sundström, Turku (FI); Annika Ålgars, Kuusisto (FI)

(73) Assignees: Olli Carpen, Espoo (FI); Minnamaija Lintunen, Turku (FI); Raija Ristamaki, Turku (FI); Jari Sundstrom, Turku (FI); Annika Algars, Kuusisto (FI); Hospital District of Southwest Finland, Turku (FI)

( * ) Notice: Subject to any disclaimer, the term of this patent is extended or adjusted under 35 U.S.C. 154(b) by 231 days.

(21) Appl. No.: 13/039,856

(22) Filed: Mar. 3, 2011

(65) Prior Publication Data
US 2011/0217296 A1 Sep. 8, 2011

Related U.S. Application Data

(60) Provisional application No. 61/310,328, filed on Mar. 4, 2010.

(51) Int. Cl.
*G01N 33/574* (2006.01)
*C12Q 1/68* (2006.01)

(52) U.S. Cl.
USPC .......................... 435/7.23; 435/6.11; 435/6.14

(58) Field of Classification Search
None
See application file for complete search history.

(56) References Cited

U.S. PATENT DOCUMENTS

| | | | |
|---|---|---|---|
| 2008/0090233 A1 | 4/2008 | Garcia et al. | |
| 2009/0017050 A1 | 1/2009 | Powell et al. | |
| 2009/0269344 A1 | 10/2009 | Siena et al. | |

FOREIGN PATENT DOCUMENTS

| | | | |
|---|---|---|---|
| WO | WO 00/20641 A1 | 4/2000 | |
| WO | WO 2007/133516 A1 | 11/2007 | |
| WO | WO 2010/022332 A1 | 2/2010 | |

OTHER PUBLICATIONS

Gaiser et al (Modern Pathology, published online Jun. 12, 2009; 22:1263-1271, IDS).*
Moroni et al (Lancet Oncology 2005; 6:279-286).*
Gaiser et al., "Comparison of automated silver enhanced in situ hybridization and fluorescense in situ hybridization for evaluation of epidermal growth factor receptor status in human glioblastomas," Modern Pathology, vol. 22, pp. 1263-1271, 2009.
Hanawa et al., "EGFR protein overexpression and gene amplification in squamous cell carcinomas of the esophagus,"Int. J. Cancer, vol. 118, pp. 1173-1180, 2006.
Hemmings et al., "Immunohistochemical expression of EGFR in colorectal carcinoma correlates with hight but not low gene amplification, as demonstrated by CISH," Pathology, vol. 41, No. 4, pp. 356-360, Jun. 2009.
Search Report issued Sep. 2, 2010, in Finnish Patent Application No. 20105210.
Miyanaga et al., "Amplification of the epidermal growth factor receptor gene in glioblastoma: An analysis of the relationship between genotype and phenotype by CISH method," Neuropathology, vol. 28, pp. 116-126, 2008.
Sholl et al., "Lung Adenocarcinoma with EGFR Amplification has Distinct Clinicopathologic and Molecular Features in Never-Smokers," Cancer Res., vol. 69, No. 21, pp. 8341-8348, Nov. 1, 2009.
Al-Kuraya et al., "HER2, TOP2A, CCND1, EGFR and C-MYC oncogene amplification in colorectal cancer", J Clin Pathol, Jul. 2007 (published online Aug. 2, 2006), vol. 60, pp. 768-772.
Al-Kuraya et al., "Prognostic relevance of gene amplifications and coamplifications in breast cancer", Cancer Res, Dec. 1, 2004, vol. 64, pp. 8534-8540.
Alvarez et al., "Expression of epidermal growth factor receptor in squamous cell carcinomas of the anal canal is independent of gene amplification", Modern Pathology, Jul. 2006 (published online Apr. 28, 2006), vol. 19, pp. 942-949.
Amann et al., "Aberrant epidermal growth factor receptor signaling and enhanced sensitivity to EGFR inhibitors in lung cancer", Cancer Res, Jan. 1, 2005, vol. 65, No. 1, pp. 226-235.
Awaya et al., "Gene amplifications and protein expression of EGFR and HER2 by chromogenic in situ hybridization and immunohistochemistry in atypical andenomatous hyperplasia and adenocarcinoma of the lung", J Clin Pathol, 2005, vol. 58, pp. 1076-1080.
Balko et al., "Gene expression patterns that predict sensitivity to epidermal growth factor receptor tyrosine kinase inhibitors in lung cancer cell lines and human lung tumors", BMC Genomics, Nov. 10, 2006, vol. 7, No. 289, 14 pages.
Bengala et al., "EGFR gene copy number, KRAS and BRAF status, PTEN and AKT factor analysis in patients with metastatic colon cancer treated with anti-EGFR monoclonal antibodies ± chemotherapy", Journal of Clinical Oncology, 2009, vol. 27, No. 15S, e15055, 1 page abstract only.
Bengala et al., "Epidermal growth factor receprot gene copy number, K-ras mutation and pathological response to preoperative cetuximab, 5-FU and radication therapy in locally advanced rectal cancer", Annals of Oncology, Mar. 2009 (published online Dec. 18, 2008), vol. 20, No. 3, pp. 469-474.
Bhargava et al., "EGFR gene amplification in breast cancer: correlation with epidermal growth factor receptor mRNA and protein expression and HER-2 status and absence of EGFR-activating mutations", Mod Pathol, 2005 (published online May 13, 2005), vol. 18, pp. 1027-1033.
Bonomi et al., "Selecting patients for treatment with epidermal growth factor tyrosine kinase inhibitors", Clin Cancer Res, Aug. 1, 2007, vol. 13, 15 Supplemental, pp. 4606S-4612S.
Bozzetti et al., "Comparison between epidermal growth factor receptor (EGFR) gene expression in primary non-small cell lung cancer (NSCLC) and in fine-needle aspitates from distant metastatic sites", Journal of Thoracic Oncology, Jan. 2008, vol. 3, No. 1, pp. 18-22.

(Continued)

*Primary Examiner* — Laura B Goddard
(74) *Attorney, Agent, or Firm* — Birch, Stewart, Kolasch & Birch, LLP

(57) ABSTRACT

The present invention relates to cancer diagnostics and therapies and to the detection of alterations in cancer cells that are diagnostic, prognostic or predictive. In particular, the present invention provides a method for detecting and analyzing whether a patient suffering from a cancer is responsive to the treatment with an EGFR inhibitor. In the method, a tissue section from a cancer sample is subjected to assays based on immunohistochemistry and enzymatic metallography.

23 Claims, 3 Drawing Sheets

(56) References Cited

OTHER PUBLICATIONS

Braut et al., "Epidermal growth factor receptor protein expression and gene amplification in normal, hyperplastic, and canceruos glottic tissue: immunohistochemical and fluorescent in situ hybridization study on tissue microarrays", Croat Med J, 2009, vol. 50, No. 4, pp. 370-379.

Buckley et al., "Epidermal growth factor receptor expression and gene copy number in conventional heptocellular carcinoma", Am J Clin Pathol, 2008, vol. 129, pp. 245-251.

Cappuzzo et al., "EGFR and HER2 gene copy number and response to first-line chemotherapy in patients with advanced non-small cell lung cancer (NSCLC)", Journal of Thoracic Oncology, May 2007, vol. 2, No. 5, pp. 423-429.

Cappuzzo et al., "EGFR FISH assay predicts for response to cetuximab in chemotherapy refractory colorectal cancer patients", Annals of Oncology, Apr. 2008 (published online Dec. 31, 2007), vol. 19, No. 4, pp. 717-723.

Cappuzzo, "EGFR FISH versus mutation: different tests, different end-points", Lung Cancer, 2008, vol. 60, pp. 160-165.

Carlson et al., "Epidermal growth factor receptor genomic variation in NSCLC patients recieving tyrosine kinase inhibitor therapy: a systematic review and meta-analysis", J Cancer Res Clin Oncol, 2009, (published online May 9, 2009), vol. 135, pp. 1483-1493.

Cascinu et al., "A combination of gefitinib and FOLFOX-4 as first-line treatment in advances colorectal cancer patients. A GISCAD multicentre phase II study . . . ", British Journal of Cancer, 2008 (published online Dec. 4, 2007), vol. 98, No. 1, pp. 71-76.

Casorzo et al., "Evaluation of 7q31 region improves the accuracy of EGFR FISH assay in non small cell lung cancer", Diagnostic Pathology, Nov. 4, 2009, vol. 4, No. 36, 8 pages.

Chang et al., "Increased epidermal growth factor receptor (EGFR) gene copy number is strongly associated with EGFR mutations and adenocarcinoma in non-small cell lung cancers: a chromogenic in situ hybridization study of 182 patients", Lung Cancer, 2008, vol. 61, pp. 328-339.

Chiang et al., "Association of epidermal growth factor receptor (EGFR) gene copy number amplification with neck lymph node metastasis in areca-associated oral carcinomas", Oral Oncology, 2008 (published online Apr. 30, 2007), vol. 44, pp. 270-276.

Cho et al., "Comparison of Her-2, EGFR and cyclin D1 in primary breast cancer and paired metastatic lymph nodes: an immunohistochemical and chromogenic in situ hybridization study", J Korean Med Sci, 2008, vol. 23, No. 6, pp. 1053-1061.

Chung et al., "Cetuximab shows activity in colorectal cancer patients with tumors that do not express the epidermal growth factor receptor by immunohistochemistry", Journal of Clinical Oncology, Mar. 20, 2005, vol. 23, No. 9, pp. 1803-1810.

Chung et al., "Increased epidermal growth factor receptor gene copy number is associated with poor prognosis in head and neck squamous cell carcinomas", Journal of Clinical Oncology, Sep. 1, 2006, vol. 24, No. 25, pp. 4170-4176.

Dacic et al., "Significance of EGFR protein expression and gene amplification in non-small cell lung carcinoma", Am J Clin Pathol, Jun. 2006, vol. 125, pp. 860-865.

Dahabreh et al., "Somatic EGFR mutation and gene copy gain as predictive biomarkers for response to tyrosine kinase inhibitors in non-small cell lung cancer", Clinical Cancer Research. Jan. 1, 2010 (published online Dec. 22, 2009), vol. 16, No. 1, pp. 291-303.

Dancer et al., "Coexpression of EGFR and HER-2 in pancreatic ductal adenocarcinoma: a comparative study using immunohistochemistry correlated with gene amplification by fluorescencent in situ hybridization", Oncology Reports, 2007, vol. 18, pp. 151-155.

Daniele et al., "Predicting gefitinib responsiveness in lung cancer by fluorescence in situ hybridization/chromogenic in situ hybridization analysis . . . ", Molecular Cancer Therapeutics, Apr. 2007, vol. 6, No. 4, pp. 1223-1229.

Dobashi et al., "Aberration of epidermal growth factor receptor expression in bone and soft-tissue tumors: protein overexpression, gene amplification and activation of downstream molecules", Modern Pathology, 2004 (published online Jul. 9, 2004), vol. 17, pp. 1497-1505.

Dziadziuszko et al., "Epidermal growth factor receptor gene copy number and protein level are not associated with outcome of non-small-cell lung cancer patients treated with chemotherapy", Annals of Oncology, Mar. 2007 (published online Nov. 2, 2006), vol. 18, No. 3, pp. 447-452.

Dziadziuszko et al., "Selecting lung cancer patients for treatment with epidermal growth factor receptor tyrosine kinase inhibitors by immunohistochemistry and fluorescence . . . ?", Clinical Cancer Research, Jul. 15, 2006, vol. 12, Supplemental 14, pp. 4409s-4415s.

El-Zammar et al., "comparison of FISH, PCR, and immunohistochemistry in assessing EGFR status in lung adenocarcinoma and correlation with clinicopathologic features", Diagn Mol Pathol, Sep. 2009, vol. 18, No. 3, pp. 133-137.

Endo et al., "Evaluation of the epidermal growth factor receptor gene mutation and copy number in non-small cell lung cancer with gefitinib therapy", Oncology Reports, 2006, vol. 16, pp. 533-541.

Fischer et al., "Utility of chromogenic in situ hybridization (CISH) for detection of EGFR amplification in glioblastoma: comparison with fluorescence in situ hybridization (FISH)", Diagn Mol Pathol, Dec. 2008, vol. 17, No. 4, pp. 227-230. .

Franchi et al., "Epidermal growth factor receptor expression and gene copy number in sinonasal intestinal type adenocarcinoma", Oral Oncology, Sep. 2009 (published online Feb. 11, 2009), vol. 45, pp. 835-838.

Freeman et al., "Copy number gains in EGFR and copy number losses in PTEN are common events in osteosarcoma tumors", Cancer, Sep. 15, 2008 (published online Aug. 14, 2008), vol. 113, No. 6, pp. 1453-1461.

Gallegos Ruiz et al., "Epidermal growth factor receptor (EGFR) gene copy number detection in non-small-cell lung cancer; a comparison of fluorescence in situ hybridization and chromogenic in situ hybridization", Histopathology, 2007, vol. 51, pp. 631-637.

Gazdar, "Activating and resistance mutations of EGFR in non-small-cell lung cancer: role in clinical response to EGFR tyrosine kinase inhibitors", Oncogene, Aug. 2009, vol. 28, Supplemental 1, pp. S24-S31 (NIH Public Access Author Manuscript, 14 pages).

Gevorgyan et al., "Epidermal Growth Factor Receptor (EGFr) status detection in correlation to objective response on cetuximab-based therapy in patients (pts) with advanced colorectal cancer (ACC)", Journal of Clinical Oncology, 2007, vol. 25, No. 18S, 21070, Abstract, 1 page.

Goncalves et al., "A polymorphism of EGFR extracellular domain is associated with progression free-survival in metastatic colorectal cancer patients receiving cetuximab-based treatment", BMC Cancer, Jun. 10, 2008, vol. 8, No. 169, 11 pages.

Hamilton, "Targeted therapy of cancer: new roles for pathologists in colorectal cancer", Modern Pathology, 2008, vol. 21, pp. S23-S30.

Han et al., "Optimization of patient selection for gefitinib in non-small cell lung cancer by combined analysis of epidermal growth factor receptor mutation, K-ras mutation, and Akt phosphorylation", Clinical Cancer Research, Apr. 15, 2006, vol. 12, No. 8, pp. 2538-2544.

Heinemann et al., "Clinical relevance of epidermal growth factor receptor- and KRAS-status in colorectal cancer patients treated with monoclonal antibodies directed against the EGFR", Cancer Treatment Reviews, 2009, vol. 35, pp. 262-271.

Helfrich et al., "Antitumor activity of the Epidermal Growth Factor Receptor (EGFR) tyrosine kinase inhibitor gefitinib (ZD1839, Iressa) in non-small cell lung cancer cell lines correlates with gene copy number . . . ", Clinical Cancer Research, Dec. 1, 2006, vol. 12, No. 23, pp. 7117-7125.

Hirsch et al., "Biomarkers for prediction of sensitivity to EGFR inhibitors in non-small cell lung cancer", Current Opinion in Oncology, 2005, vol. 17, pp. 118-122.

Hirsch et al., "Combination of EGFR gene copy number and protein expression predicts outcome for advanced non-small-cell lung cancer patients treated with gefitinib", Annals of Oncology, Apr. 2007 (published online Feb. 22, 2007), vol. 18, No. 4, pp. 752-760.

Hirsch et al., "Epidermal growth factor receptor in non-small-cell lung carcinomas: correlation between gene copy number and protein

(56) References Cited

OTHER PUBLICATIONS expression and impact on prognosis", Journal of Clinical Oncology, Oct. 15, 2003, vol. 21, No. 20, pp. 3798-3807.
Hirsch et al., "First-generation epidermal growth factor receptor inhibitors in non-small cell lung cancer: clinical impact of the epidermal growth factor receptor fluorescence in situ hybridization assay", Journal of Thoracic Oncology, Jun. 2008, vol. 3, No. 6, Supplemental 2, pp. S138-S142.
Hirsch et al., "Fluorescence in situ hybridization subgroup analysis of TRIBUTE, a phase III trial of erlotinib plus carboplatin and paclitaxel in non-small cell lung cancer", Clinical Cancer Research, Oct. 1, 2008, vol. 14, No. 19, pp. 6317-6323.
Hirsch et al., "Increased EGFR gene copy number detected by fluorescent in situ hybridization predicts outcome in non-small-cell lung cancer patients treated with cetuximab and chemotherapy", Journal of Clinical Oncology, Jul. 10, 2008, vol. 26, No. 20, pp. 3351-3357.
Hirsch et al., "Increased epidermal growth factor receptor gene copy number detected by fluorescence in situ hybridization associates with increased sensitivity to gefitinib in patients with bronchioloalveolar . . . ", Journal of Clinical Oncology, Oct. 1, 2005, vol. 23, No. 28, pp. 6838-6845.
Hirsch et al., "Molecular predictors of outcome with gefitinib in a phase III placebo-controlled study in advanced non-small-cell lung cancer", Journal of Clinical Oncology, Nov. 1, 2006, vol. 24, No. 31, pp. 5034-5042.
Hirsch et al., "Predictive value of EGFR and HER2 overexpression in advanced non-small-cell lung cancer", Oncogene, 2009, vol. 28, pp. S32-S37.
Hodgson et al., "Comparative analyses of gene copy number and mRNA expression in glioblastoma multiforme tumors and xenografts", Neuro-Oncology, Oct. 2009 (published online Jan. 12, 2009), vol. 11, pp. 477-487.
Hoff et al., "Visualization of FISH Probes by dual-color chromogenic in situ hybridization", American Journal of Clinical Pathology, 2010, vol. 133, pp. 205-211.
Italiano et al., "Cetuximab shows activity in colorectal cancer patients with tumors for which FISH analysis does not detect an increase in EGFR gene copy number", Annals of Surgical Oncology, 2008 (published online Nov. 7, 2007), vol. 15, No. 2, pp. 649-654.
Italiano et al., "Comparison of the epidermal growth factor receptor gene and protein in primary non-small-cell-lung cancer and metastatic sites: implications for treatment with EGFR-inhibitors", Annals of Oncology, Jun. 2006 (published online Mar. 8, 2006), vol. 17, No. 6, pp. 981-985.
Italiano et al., "EGFR and KRAS status of primary sarcomatoid carcinomas of the lung: implications for anti-EGFR treatment of a rare lung malignancy", Int J Cancer, 2009 (published online Jun. 2, 2009), vol. 125, pp. 2479-2482.
Järvelä et al., "Amplification of the epidermal growth factor receptor in astrocytic tumours by chromogenic in situ hybridization: association with clinicopathological features and patient survival", Neuropathology and Applied Neurobiology, 2006, vol. 32, pp. 441-450.
Jeon et al., "Clinicopathologic features and prognostic implications of epidermal growth factor receptor (EGFR) gene copy number and protein expression in non-small cell lung cancer", Lung Cancer, 2006 vol. 54, pp. 387-398.
Jimeno et al., "Coordinated epidermal growth factor receptor pathway gene overexpression predicts epidermal growth factor receptor inhibitor sensitivity in pancreatic cancer", Cancer Research, Apr. 15, 2008, vol. 68, No. 8, pp. 2841-2849.
John et al., "Overview of molecular testing in non-small-cell lung cancer: mutational analysis, gene copy number, protein expression and other biomarkers of EGFR for the prediction of response to tyrosine kinase inhibitors", Oncogene, 2009, vol. 28, pp. S14-S23.
Kalish et al., "Deregulated cyclin D1 expression is associated with decreased efficacy of the selective epidermal growth factor receptor tyrosine kinase inhibitor gefitinib in head and neck squamous cell carcinoma cell lines", Clinical Cancer Research, Nov. 15, 2004, vol. 10, pp. 7764-7774.
Kanteti et al., "MET, HGF, EGFR, and PXN gene copy number in lung cancer using DNA extracts from FFPE archival samples and prognostic significance", J Environ Pathol Toxicol Oncol, 2009, vol. 28, No. 2, pp. 89-98 (NIH Public Access Author Manuscript, 14 pages).
Kersting et al., "Gene dosage PCR and fluorescence in situ hybridization reveal low frequency of egfr amplifications despite protein overexpression in invasive breast carcinoma", Laboratory Investigation, 2004 (published online Mar. 15, 2004), vol. 84, pp. 582-587.
Kersting et al., "Pitfalls in immunohistochemical assessment of EGFR expression in soft tissue sarcomas", J Clin Pathol, 2006, vol. 59, pp. 585-590.
Khambata-Ford et al., "Analysis of potential predictive markers of cetuximab benefit in BMS099, a phase III study of cetuximab and first-line taxane/carboplatin in advanced . . . ", Journal of Clinical Oncology, Feb. 20, 2010 (published online Jan. 25, 2010), vol. 28, No. 6, pp. 918-927.
Kim et al., "EGFR in gastric carcinomas: prognostic significance of protein overexpression and high gene copy number", Histopathology, 2008, vol. 52, pp. 738-746.
Kim et al., "High tumour islet macrophage infiltration correlates with improved patient survival but not with EGFR mutations, gene copy number or protein expression in resected non-small cell lung cancer", British Journal of Cancer, 2008 (published online Feb. 19, 2008), vol. 98, No. 6, pp. 1118-1124.
Kimura et al., "A proposal for diagnostically meaningful criteria to classify increased epidermal growth factor receptor and c-erbB-2 gene copy numbers in gastric carcinoma, based on correlation of fluorescence in situ hybridization . . . ", Virchows Arch, 2004, vol. 445, pp. 255-262.
Kirkegaard et al., "Amplified in breast cancer 1 in human epidermal growth factor receptor—positive tumors of tamoxifen-treated breast cancer patients", Clinical Cancer Research, Mar. 1, 2007, vol. 13, No. 5, pp. 1405-1411.
Koynova et al., "Tissue microarray analysis of EGFR and HER2 oncogene copy number alterations in squamous cell carcinoma of the larynx", J Cancer Res Clin Oncol, 2005 (published online Dec. 8, 2004), vol. 131, pp. 199-203.
Kubo et al., "MET gene amplification or EGFR mutation activate MET in lung cancers untreated with EGFR tyrosine kinase inhibitors", Int J Cancer, Apr. 15, 2009, vol. 124, No. 8, pp. 1778-1784 (NIH public access author manuscript, 17 pages).
Lambros et al., "Chromogenic and fluorescent in situ hybridization in breast cancer", Human Pathology, 2007, vol. 38, pp. 1105-1122.
Laurent-Puig et al., "Analysis of PTEN, BRAF, and EGFR status in determining benefit from cetuximab therapy in wild-type KRAS metastatic colon cancer", Journal of Clinical Oncology, Dec. 10, 2009 (published online Nov. 2, 2009), vol. 27, No. 35, pp. 5924-5930.
Le Tourneau et al., "Progress and challenges in the identification of biomarkers for EGFR and VEGFR targeting anticancer agents", Drug Resistance Updates, 2008, vol. 11, pp. 99-109.
Lee et al., "Detection of HER-2 and EGFR gene amplification using chromogenic in-situ hybridization technique in ovarian tumors", Appl Immunohistochem Mol Morphol, Jan. 2010, vol. 18, No. 1, pp. 69-74.
Lee et al., "Epidermal growth factor receptor status in anaplastic thyroid carcinoma", J Clin Pathol, 2007 (published online Nov. 1, 2006), vol. 60, pp. 881-884.
Lee et al., "Impact of epidermal growth factor receptor (EGFR) kinase mutations, EGFR gene amplifications, and KRAS mutations on survival of pancreatic adenocarcinoma", Cancer, Apr. 15, 2007 (published online Mar. 12, 2007), vol. 109, No. 8, pp. 1561-1569.
Lee et al., "Protein overexpression and gene amplification of epidermal growth factor receptor in nonsmall cell lung carcinomas: Comparison of four commercially available antibodies by immunohistochemistry . . . ", Lung Cancer, 2010, vol. 68, pp. 375-382.
Li et al., "EGFR mutations in lung adenocarcinomas: clinical testing experience and relationship to EGFR gene copy number and immunohistochemical expression", Journal of Molecular Diagnostics, May 2008, vol. 10, No. 3, pp. 242-248.

(56) References Cited

OTHER PUBLICATIONS

Liang et al., "Analysis of EGFR, HER2, and TOP2A gene status and chromosomal polysomy in gastric adenocarcinoma from Chinese patients", BMC Cancer, Dec. 6, 2008, vol. 8, No. 363, 12 pages.

Lievre et al., "Facteurs prédictifs de réponse aux traitements anti-REGF dans le cancer colorectal", Bull Cancer, Jan. 2008, vol. 95, No. 1, pp. 133-140.

Lopes et al., "EGFR and gastrointestinal stromal tumor: an immunohistochemical and FISH study of 82 cases", Modern Pathology, 2007 (published online Jul. 20, 2007), vol. 20, pp. 990-994.

Lopez-Gines et al., "New pattern of EGFR amplification in glioblastoma and the relationship of gene copy number with gene expression profile", Modern Pathology, 2010 (published online Mar. 19, 2010), vol. 23, pp. 856-865.

Macarenco et al., "Salivary gland-type lung carcinomas: an EGFR immunohistochemical, molecular genetic, and mutational analysis study", Modern Pathology, 2008 (published online Jun. 27, 2008), vol. 21, pp. 1168-1175.

Mancuso et al., "EGFR, DCC, and K-RAS mutations as predictive factors for cetuximab sensitivity in metastatic colorectal cancer (mCRC)", Journal of Clinical Oncology, 2008, vol. 26, No. 15S, 4128, Abstract 1 page.

Marks et al., "Epidermal growth factor receptor (EGFR) expression in prostatic adenocarcinoma after hormonal therapy: a fluorescence in situ hybridization and immunohistochemical analysis", The Prostate, 2008 (published online Apr. 11, 2008), vol. 68, pp. 919-923.

Marquez et al., "Evaluation of epidermal growth factor receptor (EGFR) by chromogenic in situ hybridization (CISH) and immunohistochemistry (IHC) in archival gliomas using bright-field microscopy", Diagn Mol Pathol, Mar. 2004, vol. 13, No. 1, pp. 1-8.

Meriggi et al., "Anti-EGFR therapy in colorectal cancer: how to choose the right patient", Current Drug Targets, Oct. 2009, vol. 10, No. 10, pp. 1033-1040.

Merlino et al., "Elevated epidermal growth factor receptor gene copy number and expression in a squamous carcinoma cell line", The Journal of Clinical Investigation, Inc., Mar. 1985, vol. 75, pp. 1077-1079.

Milano et al., "Epidermal growth factor receptor (EGFR) status and K-RAS mutations in colorectal cancer", Annals of Oncology, Dec. 2008 (published online Jul. 15, 2008), vol. 19, No. 12, pp. 2033-2038.

Moch et al., "EGF-r gene copy number changes in renal cell carcinoma detected by fluorescence in situ hybridization", Journal of Pathology, 1998, vol. 184, pp. 424-429.

Modrek et al., "oncogenic activating mutations are associated with local copy gain", Molecular Cancer Research, Aug. 2009, vol. 7, No. 8, pp. 1244-1252.

Mrhalova et al., "Epidermal growth factor receptor—its expression and copy numbers of EGFR gene in patients with head and neck squamous cell carcinomas", Neoplasma, 2005, vol. 52, No. 4, pp. 338-343.

Neyns et al., "Stratified phase II trial of cetuximab in patients with recurrent high-grade glioma", Annals of Oncology, Sep. 2009 (published online Jun. 2, 2009), vol. 2, No. 9, pp. 1596-1603.

Okuda et al., "Epidermal growth factor receptor gene mutation, amplification and protein expression in malignant pleural mesothelioma", J Cancer Res Clin Oncol, 2008 (published online Apr. 8, 2008), vol. 134, pp. 1105-1111.

Ooi et al., "Gene amplification of Myc and its coamplification with ERBB2 and EGFR in gallbladder adenocarcinoma", Anticancer Res, 2009, vol. 29, pp. 19-26.

Park et al., "EGFR gene and protein expression in breast cancers", EJSO the Journal of Cancer Surgery, 2007 (published online Mar. 19, 2007), vol. 33, pp. 956-960.

Park et al., "EGFR gene copy number in adenocarcinoma of the lung by FISH analysis: investigation of significantly related factors on CT, FDG-PET, and histopathology", Lung Cancer, 2009, vol. 64, pp. 179-186

Peled et al., "Predictive and prognostic markers for epidermal growth factor receptor inhibitor therapy in non-small cell lung cancer", Therapeutic Advances in Medical Oncology, Nov. 2009, vol. 1, No. 3, pp. 137-144.

Pennell et al., "Assessing the roles of EGFR gene copy number, protein expression and mutation in predicting outcomes in non-small-cell lung cancer after treatment with EGFR inhibitors", Biomarkers Med, 2007, vol. 1, No. 1, pp. 203-207.

Personeni et al., "Clinical usefulness of Egfr gene copy number as a predictive marker in colorectal cancer patients treated with cetuximab: a fluorescent in situ hybridization study", Clin Cancer Res, Sep. 15, 2008, vol. 14, No. 18, pp. 5869-5876.

Personeni, "Epidermal growth factor receptor gene copy number in esophageal cancer and outcome prediction to gefitinib: does intratumoral heterogeneity matter?", Journal of Clinical Oncology, Dec. 1, 2006, vol. 24, No. 34, pp. 5465.

Pinter et al., "Epidermal growth factor receptor (EGFR) high gene copy number and activating mutations in lung adenocarcinomas are not consistently accompanied by positivity for EGFR protein by standard immunohistochemistry", Journal of Molecular Diagnostics, Mar. 2008, vol. 10, No. 2, pp. 160-168.

Pugh et al., "Correlations of EGFR mutations and increases in EGFR and HER2 copy number to gefitinib response in a retrospective analysis of lung cancer patients", BMC Cancer, Jul. 13, 2007, vol. 7, No. 128, 12 pages.

Rakosy et al., "EGFR gene copy number alterations in primary cutaneous malignant melanomas are associated with poor prognosis", Int J Cancer, 2007, vol. 121, pp. 1729-1737.

Reis-Filho et al., "Metaplastic breast carcinomas exhibit EGFR, but not HER2, gene amplification and overexpression: immunohistochemical and chromogenic in situ hybridization analysis", Breast Cancer Research, 2005, vol. 7, No. 6, pp. R1028-R1035.

Rosell et al., "Usefulness of predictive tests for cancer treatment", Bull Cancer, 2006, vol. 93, No. 8, pp. E101-E108.

Rydén et al., "Epidermal growth factor receptor and vascular endothelial growth factor receptor 2 are specific biomarkers in triple-negative breast cancer. Results from a controlled randomized trial . . . ", Breast Cancer Res Treat, 2010 (published online Feb. 5, 2010), vol. 120, pp. 491-498.

Ryott et al., "EGFR protein overexpression and gene copy number increases in oral tongue squamous cell carcinoma", European Journal of Cancer, 2009 (published online Mar. 28, 2009), vol. 45, pp. 1700-1708.

Sakurada et al., "Predictive biomarkers for EGFR therapy", IDrugs, Jan. 2009, vol. 12, No. 1, pp. 34-38.

Sartore-Bianchi et al., "Integrated molecular dissection of the epidermal growth factor receptor (EGFR) oncogenic pathway to predict response to EGFR-targeted monoclonal antibodies in metastatic colorectal cancer", Targ Oncol, 2010 (published online Apr. 11, 2010), vol. 5, pp. 19-28.

Sartore-Bianchi, "Epidermal growth factor receptor gene copy number and clinical outcome of metastatic colorectal cancer treated with panitumumab", Journal of Clinical Oncology, Aug. 1, 2007, vol. 25, No. 22, pp. 3238-3245.

Sauer et al., "Demonstration of EGFR gene copy loss in colorectal carcinomas by fluorescence in situ hybridization (FISH): a surrogate marker for sensitivity to specific anti-EGFR therapy?", Histopathology, 2005, vol. 47, pp. 560-564.

Sauer et al., "EGFR gene copy number heterogeneity in fine-needle aspiration cytology from breast carcinomas determined by chromogenic in situ hybridization", Diagnostic Cytopathology, 2005, vol. 33, No. 4, pp. 228-232.

Sauter et al., "Patterns of epidermal growth factor receptor amplification in malignant gliomas", Am J Pathol, Apr. 1996, vol. 148, No. 4, pp. 1047-1053.

Savic et al., "Comprehensive epidermal growth factor receptor gene analysis from cytological specimens of non-small-cell lung cancers", British Journal of Cancer, 2008 (published online Dec. 18, 2007), vol. 98, No. 1, pp. 154-160.

Scartozzi et al., "Epidermal growth factor receptor (EGFR) gene copy number (GCN) correlates with clinical activity of irinotecan-

(56) References Cited

OTHER PUBLICATIONS cetuximab in K-RAS wild-type colorectal cancer: a fluorescence in situ (FISH) and chromogenic . . . ", BMC Cancer, Aug. 27, 2009, vol. 9, No. 303, 8 pages.

Schlomm et al., "Clinical significance of epidermal growth factor receptor protein overexpression and gene copy number gains in prostate cancer", Clinical Cancer Research, Nov. 15, 2007, vol. 13, No. 22, pp. 6579-6584.

Schneider et al., "Epidermal growth factor receptor-related tumor markers and clinical outcomes with erlotinib in non-small cell lung cancer: an analysis of patients from German centers in the TRUST study", Journal of Thoracic Oncology, Dec. 2008, vol. 3, No. 12, pp. 1446-1453.

Shafizadeh et al., "Epidermal growth factor receptor and HER-2/neu status by immunohistochemistry and fluorescence in situ hybridization in adenocarcinomas of the biliary tree and gallbladder", Human Pathology, 2010, vol. 41, pp. 485-492.

Sheu et al., "Functional genomic analysis identified epidermal growth factor receptor activation as the most common genetic event in oral squamous cell carcinoma", Cancer Research, Mar. 15, 2009, vol. 69, No. 6, pp. 2568-2576 (published online Mar. 10, 2009).

Sholl et al., "Validation of chromogenic in situ hybridization for detection of EGFR copy number amplification in nonsmall cell lung carcinoma", Modern Pathology, 2007 (published online Aug. 3, 2007), vol. 20, pp. 1028-1035.

Skacel et al., "Aneusomy of chromosomes 7, 8, and 17 and amplification of HER-2/neu and epidermal growth factor receptor in Gleason score 7 prostate carcinoma: a differential fluorescent in situ hybridization study of Gleason . . . ", Human Pathology, Dec. 2001, vol. 32, No. 12, pp. 1392-1397.

Sone et al., "Comparative analysis of epidermal growth factor receptor mutations and gene amplification as predictors of gefitinib efficacy in Japanese patients with nonsmall cell lung cancer", Cancer, 2007 (published online Mar. 26, 2007), vol. 109, No. 9, pp. 1836-1844.

Spindler et al., "Epidermal growth factor receptor analyses in colorectal cancer: a comparison of methods", International Journal of Oncology, 2006, vol. 29, pp. 1159-1165.

Stadlmann et al., "Epithelial growth factor receptor status in primary and recurrent ovarian cancer", Modern Pathology, 2006, vol. 19, pp. 607-610.

Tang et al., "Epidermal growth factor receptor abnormalities in the pathogenesis and progression of lung adenocarcinomas", Cancer Prevention Research, Aug. 2008, vol. 1, No. 3, pp. 192-200.

Taron et al., "Activating mutations in the tyrosine kinase domain of the epidermal growth factor receptor are associated with improved survival in gefitinib-treated chemorefractory lung adenocarcinomas", Clinical Cancer Research, Aug. 15, 2005, vol. 11, No. 16, pp. 5878-5885.

Tatematsu et al., "Epidermal growth factor receptor mutations in small cell lung cancer", Clinical Cancer Research, Oct. 1, 2008, vol. 14, No. 19, pp. 6092-6096.

Temam et al., "Epidermal growth factor receptor copy number alterations correlate with poor clinical outcome in patients with head and neck squamous cancer", Journal of Clinical Oncology, Jun. 1, 2007, vol. 25, No. 16, pp. 2164-2170.

Tiseo et al., "Predictors of gefitinib outcomes in advanced non-small cell lung cancer (NSCLC): study of a comprehensive panel of molecular markers", Lung Cancer, 2010, vol. 67, pp. 355-360.

Toschi et al., "Understanding the new genetics of responsiveness to epidermal growth factor receptor tyrosine kinase inhibitors", The Oncologist, 2007, vol. 12, pp. 211-220.

Toth et al., "Analysis of EGFR gene amplification, protein overexpression and tyrosine kinase domain mutation in recurrent glioblastoma", Pathol Oncol Res, 2009 (published online Aug. 28, 2008), vol. 15, pp. 225-229.

Toyama et al., "Frequently increased epidermal growth factor receptor (EGFR) copy numbers and decreased BRCA1 mRNA expression in Japanese triple-negative breast cancers", BMC Cancer, Oct. 25, 2008, vol. 8, No. 309, 12 pages.

Tsiambas et al., "Chromogenic in situ hybridization analysis of EGFR gene copies in colon adenocarcinoma based on intra-operative imprints and tissue microarrays", J Gastrointestin Liver Dis, Sep. 2009, vol. 18, No. 3, pp. 293-298.

Tsiambas et al., "Simultaneous EGFR and VEGF alterations in non-small cell lung carcinoma based on tissue microarrays", Cancer Informatics, 2007, vol. 3, pp. 275-284.

Udart et al., "Chromosome 7 aneusomy. A marker for metastatic melanoma? Expression of the epidermal growth factor receptor gene and chromosome 7 aneusomy in nevi, primary malignant melanomas and metastases", Neoplasia, 2001, vol. 3, No. 3, pp. 245-254.

Uramoto et al., "Which biomarker predicts benefit from EGFR-TKI treatment for patients with lung cancer?", British Journal of Cancer, 2007 (published online Feb. 27, 2007), vol. 96, No. 6, pp. 857-863.

Varella-Garcia et al., "EGFR and HER2 genomic gain in recurrent non-small cell lung cancer after surgery: impact on outcome to treatment with gefitinib and assoc. with EGFR and KRAS . . . ", J Thorac Oncol, 2009, vol. 4, pp. 318-325 (NIH public access author manuscript 16 pages).

Varella-Garcia et al., "EGFR fluorescence in situ hybridisation assay: guidelines for application to non-small-cell lung cancer", J Clin Pathol, 2009, vol. 62, pp. 970-977.

Varella-Garcia, "Stratification of non-small cell lung cancer patients for therapy with epidermal growth factor receptor inhibitors: the EGFR fluorescence in situ hybridization assay", Diagnostic Pathology, Aug. 15, 2006, vol. 1, No. 19, 10 pages.

Vermeij et al., "Genomic activation of the EGFR and HER2-neu genes in a significant proportion of invasive epithelial ovarian cancers", BMC Cancer, Jan. 8, 2008, vol. 8, No. 3, 9 pages.

Viana-Pereira et al., "Analysis of EGFR overexpression, EGFR gene amplification and the EGFRvIII mutation in Portuguese high-grade gliomas", Anticancer Research, 2008, vol. 28, pp. 913-920.

Vidal et al., "Fluorescence in situ hybridization gene amplification analysis of EGFR and HER2 in patients with malignant salivary gland tumors treated with lapatinib", Head Neck, Aug. 2009, vol. 31, No. 8, pp. 1006-1012 (NIH public access author manuscript, 10 pages).

Wang et al., "Epidermal growth factor protein expression and gene amplification in small call carcinoma of the urinary bladder", Clinical Cancer Research, Feb. 1, 2007, vol. 13, No. 3, pp. 953-957.

Wang et al., "Epidermal growth factor receptor protein expression and gene amplification in the chemorefractory metastatic embryonal carcinoma", Modern Pathology, Jan. 2009 (published online Jul. 25, 2008), vol. 22, pp. 7-12.

Wei et al., "EGFR expression as an ancillary tool for diagnosing lung cancer in cytology specimens", Modern Pathology, 2007 (published online Jul. 20, 2007), vol. 20, pp. 905-913.

Williams et al., "Genetic and expression analysis of HER-2 and EGFR genes in salivary duct carcinoma: empirical and therapeutic significance", Clinical Cancer Research, Apr. 15, 2010 (published online Apr. 14, 2010), vol. 16, No. 8, pp. 2266-2274.

Wilmore-Payne et al., "Detection of epidermal growth factor receptor and human epidermal growth factor receptor 2 activating mutations in lung adenocarcinoma by high-resolution melting amplicon analysis: correlation with gene copy number . . . ", Human Pathology, 2006, vol. 37, pp. 755-763.

Wong et al., "Increased expression of the epidermal growth factor receptor gene in malignant gliomas is invariably associated with gene amplification", Proc Natl Acad Sci USA, Oct. 1987, vol. 84, pp. 6899-6903.

Yamatodani et al., "Epidermal growth factor receptor status and persistent activation of Akt and p44/42 MAPK pathways correlate with the effect of cetuximab in head and neck and colon cancer cell lines", J Cancer Res Clin Oncol, 2009 (published online Sep. 2008), vol. 135, pp. 395-402.

Yan et al., "Pharmacogenetics and pharmacogenomics in oncology therapeutic antibody development", Biotechniques, Oct. 2005, vol. 39, pp. 565-568.

(56) References Cited

OTHER PUBLICATIONS

Yatabe et al., "Epidermal growth factor receptor gene amplification is acquired in association with tumor progression of EGFR-mutated lung cancer", Cancer Research, Apr. 1, 2008, vol. 68, No. 7, pp. 2106-2111.

Yoo et al., "Reliability of chromogenic in situ hybridization for epidermal growth factor receptor gene copy number detection in non-small-cell lung carcinomas: a comparison with fluorescence in situ hybridization study", Lung Cancer, 2010, vol. 67, pp. 301-305.

Zakowski et al., "Morphologic features of adenocarcinoma of the lung predictive of response to the epidermal growth factor receptor kinase inhibitors erlotinib and gefitinib", Arch Pathol Lab Med, Mar. 2009, vol. 133, pp. 470-477.

Zhu et al., "Role of KRAS and EGFR as biomarkers of response to erlotinib in National Cancer Institute of Canada Clinical Trials Group Study BR.21", Journal of Clinical Oncology, Sep. 10, 2008 (published online Jul. 14, 2008), vol. 26, No. 26, pp. 4268-4275.

Zlobec et al., "Assessment of mean EGFR gene copy number is a highly reproducible method for evaluating FISH in histological and cytological cancer specimens", Lung Cancer, 2010, vol. 68, pp. 192-197.

* cited by examiner

METHOD FOR SELECTING PATIENTS FOR TREATMENT WITH AN EGFR INHIBITOR

CROSS REFERENCE TO RELATED APPLICATIONS

This nonprovisional application claims the benefit of U.S. Provisional Application No. 61/310,328 filed on Mar. 4, 2010. The entire contents of the above application is hereby incorporated by reference.

FIELD OF THE INVENTION

The present invention relates to cancer diagnostics and therapies and in particular to the detection of alterations in cancer cells that are diagnostic, prognostic and/or predictive and which can be used for selecting patients suffering from cancer that are responsive to treatment with an EGFR inhibitor.

BACKGROUND OF THE INVENTION

Epidermal Growth Factor Receptor (EGFR) is a member of the type 1 tyrosine kinase family of growth factor receptors, which play critical roles in cellular growth, differentiation, and survival. Activation of these receptors typically occurs via specific ligand binding, resulting in hetero- or homodimerization between receptor family members, with subsequent autophosphorylation of the tyrosine kinase domain. This activation triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

The EGFR signaling pathway is activated in several cancers, such as colorectal cancer (CRC), non-small cell lung cancer (NSCLC), head and neck cancer and gliomas. Activation may occur by multiple mechanisms, including activating mutations in the EGFR protein, or EGFR overexpression, typically due to increased EGFR gene copy number. The EGFR protein expression can be assessed semi quantitatively by immunohistochemistry. Gene copy number can be evaluated by several methods, including in-situ hybridization and gene mutations can be detected by several methods including direct sequencing.

EGFR antibodies in clinical use (e.g., cetuximab (ERBITUX™) and panitumumab (VECTIBIX™)) bind to the extracellular domain of the EGFR. This receptor domain includes the ligand binding site and these antibodies are believed to block ligand binding; thereby, disrupting EGFR signaling. As a result of the therapeutic utility of such EGFR antibodies, many subsequent studies have focused on the production of antibodies (or other binding molecules) specific for the EGFR extracellular domain (see, e.g., U.S. Pat. Nos. 5,459,061, 5,558,864, 5,891,996, 6,217,866, 6,235,883, 6,699,473, and 7,060,808; European Pat. Nos. EP0359282 and EP0667165).

Approximately 10-20% of unselected CRC patients respond to anti-EGFR antibody therapy. In CRC, as in many other cancers, neither the diagnostic characteristics of the tumor nor the degree of EGFR expression evaluated by immunohistochemistry, are thought to correlate with clinical response to anti-EGFR antibodies, such as cetuximab, matuzumab (hMab 425) or panitumumab. Currently, therefore, most treated patients are exposed to the risk of ineffective therapy with undesired side effects.

KRAS gene mutational status can predict the response to the anti-EGFR monoclonal antibodies cetuximab and panitumumab (Allegra, 2009). Tumors harbouring activating mutations of KRAS, a signaling molecule downstream of EGFR, do no benefit from anti-EGFR therapy (Linardou, 2008). In KRAS wild type (WT) patients, on the other hand, the addition of cetuximab to cytotoxic treatment improves the response rates with 16 to 24% compared to cytotoxic therapy alone. About 40% of the KRAS WT patients are non-responders to combination therapy (Bokemeyer, 2009; Van Cutsem, 2009) and a significantly larger fraction of patients are non-responders to EGFR antibody monotherapy (Amado, 2008).

In addition to KRAS mutations, changes in other molecules downstream of EGFR, in particular BRAF gene mutations, PIK3CA mutations and loss of expression of the PTEN tumor suppressor protein appear to associate with resistance to anti-EGFR treatment (Laurent-Puig, 2009; Siena, 2009). Accordingly, BRAF testing was recently included in the NCCN Clinical Guidelines in Oncology for Colon Cancer and Rectal Cancer (Engstrom, 2009). However, even the combination of these tests is likely to identify only a minority of non-responsive KRAS WT patients (Laurent-Puig, 2009).

In previous studies the EGFR protein expression level assessed by immunohistochemistry (IHC) has not correlated with response to anti-EGFR antibody treatment (Cunningham, 2004; Saltz, 2004; Chung, 2005). Instead, an increased EGFR gene copy number (GCN) has in some studies shown an association with a favorable response among KRAS WT patients (Sartore-Bianchi, 2007; Cappuzzo, 2008; Lievre, 2006; Moroni, 2005). Fluorescence in situ hybridization (FISH) technique has been used in most previous studies (Moroni, 2005; Cappuzzo, 2008; Personeni, 2008; Scartozzi, 2009; Sartore-Bianchi, 2007). The FISH results are challenging to interpret and the lack of standardization of analytical method and scoring systems may partly explain why the EGFR GCN evaluation has not been incorporated into the clinical practice yet. In fact, the current NCCN colorectal cancel guidelines do not recommend routine EGFR testing, and state that no patient should be either considered or excluded from cetuximab or panitumumab therapy on the basis of EGFR test results (Engstrom, 2009).

In summary, there is a need to explain the differential response in patients to anti-EGFR monoclonal antibodies and to develop a strategy to identify cancer patients such as colorectal cancer patients likely to benefit from or be responsive to anti-EGFR antibody therapy.

US2008/0090233 (Garcia et al.) discloses a method to select a cancer patient who is predicted to benefit or not benefit from therapeutic administration of an EGFR inhibitor. The method is based on the detection of a level of amplification and polysomy of the EGFR gene and the HER2 gene. The assay for detecting gene copy number is based on fluorescence in situ hybridization (FISH).

US2009/0269344 (Siena et al.) discloses an in vitro method for detecting and analyzing whether a patient suffering from a cancer, which overexpresses EGFR, responds positively to the administration of an anti-EGFR antibody. The method comprises the steps of determining the EGFR gene copy number in tumor cells obtained from a patient and selecting said patient for administration with said anti-EGFR antibody, if the tumor cells of the patient display an amplified copy number of the EGFR gene. The assay for detecting gene copy number is based on fluorescence in situ hybridization (FISH).

Hanawa et al. (2006) analyzed EGFR protein expression with IHC and EGFR gene copy number with FISH in cancer samples of esophagus.

Hemmings et al. (2009) analyzed EGFR protein expression using IHC in colorectal cancer samples. They also used CISH to detect gene copy number of EGFR.

Sholl et al. (2009) used IHC to detect EGFR protein in lung adenocarcinoma samples. They also used FISH and CISH to detect EGFR gene copy number and correlated FISH analysis results to those of CISH.

Gaiser et al. (2009) compared the concordance between SISH and FISH methods in glioblastoma patients and used EGFR IHC to detect EGFR protein.

Miyanaga et al. (2008) used IHC to detect EGFR protein expression and CISH method to analyze EGFR gene copy number.

However, none of the above-mentioned prior art documents discloses enzymatic metallography method (e.g. SISH) to detect EGFR GCN and EGFR IHC to select cancer patients for EGFR inhibitor treatment. Further, the cited prior art do not teach that it would be advantageous to determine the area of highest expression of EGFR in a tumor sample by IHC, and then use said area of highest expression in enzymatic metallography to determine gene copy number of EGFR gene or chromosome 7. This approach renders results more reliable and thus EGFR GCN evaluation may become part of clinical practice.

SUMMARY OF THE INVENTION

The present invention demonstrates that epidermal growth factor receptor (EGFR) gene copy number (GCN) analysis in areas of highest EGFR immunoreactivity, preferably by silver in situ hybridization (SISH), predicts the efficacy of anti-EGFR therapy in cancers, preferably in colorectal cancer as a single diagnostic test, or in combination with determining the presence or absence of KRAS mutation and the EGFR GCN and separating responders and non-responders to anti-EGFR treatment.

In one aspect the invention concerns a method for detecting and analyzing whether a patient suffering from a cancer is responsive or non-responsive to the treatment with an EGFR inhibitor, the method comprising the steps of determining in a tissue section from a tumor sample obtained from said patient (i) the expression level of an EGFR protein in said tissue section by immunohistochemistry (IHC), and (ii) the level of EGFR gene copy number or the level of copy number of chromosome 7 by enzymatic metallography, wherein the area of highest expression of EGFR in a tissue section from said tumor sample is determined by IHC based on staining intensity, and said area of highest expression in the tumor sample is used in enzymatic metallography to determine gene copy number of EGFR gene or chromosome 7; and selecting said patient for treatment with said EGFR inhibitor, if the tumor sample of said patient displays expression of EGFR protein and an amplified copy number of the EGFR gene or chromosome 7.

In an embodiment same tissue section from said tumor sample is used in IHC and in enzymatic metallography.

In an embodiment consecutive tissue sections from said tumor sample are used in IHC and in enzymatic metallography.

In an embodiment the level of EGFR gene copy number or the level of copy number of chromosome 7 is determined as ratio of the number of EGFR genes or chromosome 7 per nucleus.

In an embodiment the enzymatic metallography is silver in situ hybridization (SISH) analysis.

In an embodiment the patient is selected for the treatment with the EGFR inhibitor, if the level of EGFR gene copy number or the level of copy number of chromosome 7 is statistically similar to or greater than the threshold level of EGFR gene copy number or level of copy number of chromosome 7 that has been correlated with response to the treatment with the EGFR inhibitor.

In an embodiment the patient is not selected for the treatment with the EGFR inhibitor, if the level of EGFR gene copy number or the level of copy number of chromosome 7 is statistically less than he threshold level of EGFR gene copy number or level of copy number of chromosome 7 that has been correlated with response to the treatment with the EGFR inhibitor.

In an embodiment the patient is selected for the treatment with the EGFR inhibitor, if the level of EGFR gene copy number is ≥4.0 or the level of copy number of chromosome 7 in nucleus is ≥4.5.

In an embodiment a cancer is colorectal cancer, lung cancer, head and neck cancer, or glioma.

In an embodiment IHC is performed with an anti-EGFR antibody. Preferably, the EGFR staining intensity and staining pattern of the antibody is the same as with the anti-EGFR antibody 5B7 directed to an intracellular epitope of the EGFR.

In an embodiment the antibody binds to an intracellular domain of the EGFR.

In an embodiment the antibody is clone 5B7 or 3C6.

In an embodiment the EGFR inhibitor is an antibody or a kinase inhibitor.

In an embodiment the antibody is cetuximab (mAb c225), matuzumab (mAb h425) or panitumumab (mAb ABX).

In an embodiment the kinase inhibitor is erlotinib or gefitinib.

In an embodiment the method further comprises the step of determining the presence or absence of KRAS mutation in said tumor sample.

In an embodiment the method further comprises the step of determining the presence or absence of a mutated EGFR gene or EGFR protein in the tumor sample.

In an embodiment the tissue section is prepared on a microscope slide.

In an embodiment the tissue section is ≤5 μm thick.

In an embodiment steps (i) and (ii) are performed with an automated processing apparatus.

In one aspect, the invention concerns a method of treating a patient suffering from a cancer comprising the steps of obtaining a tumor sample from said patient, analyzing said sample by the method according to claim 1 and administering an EGFR inhibitor to said patient, if said patient was selected for treatment with said EGFR inhibitor.

In one aspect the invention concerns an assay kit comprising means for performing the method according to claim 1.

DETAILED DESCRIPTION OF THE INVENTION

Definitions

Figure 1:
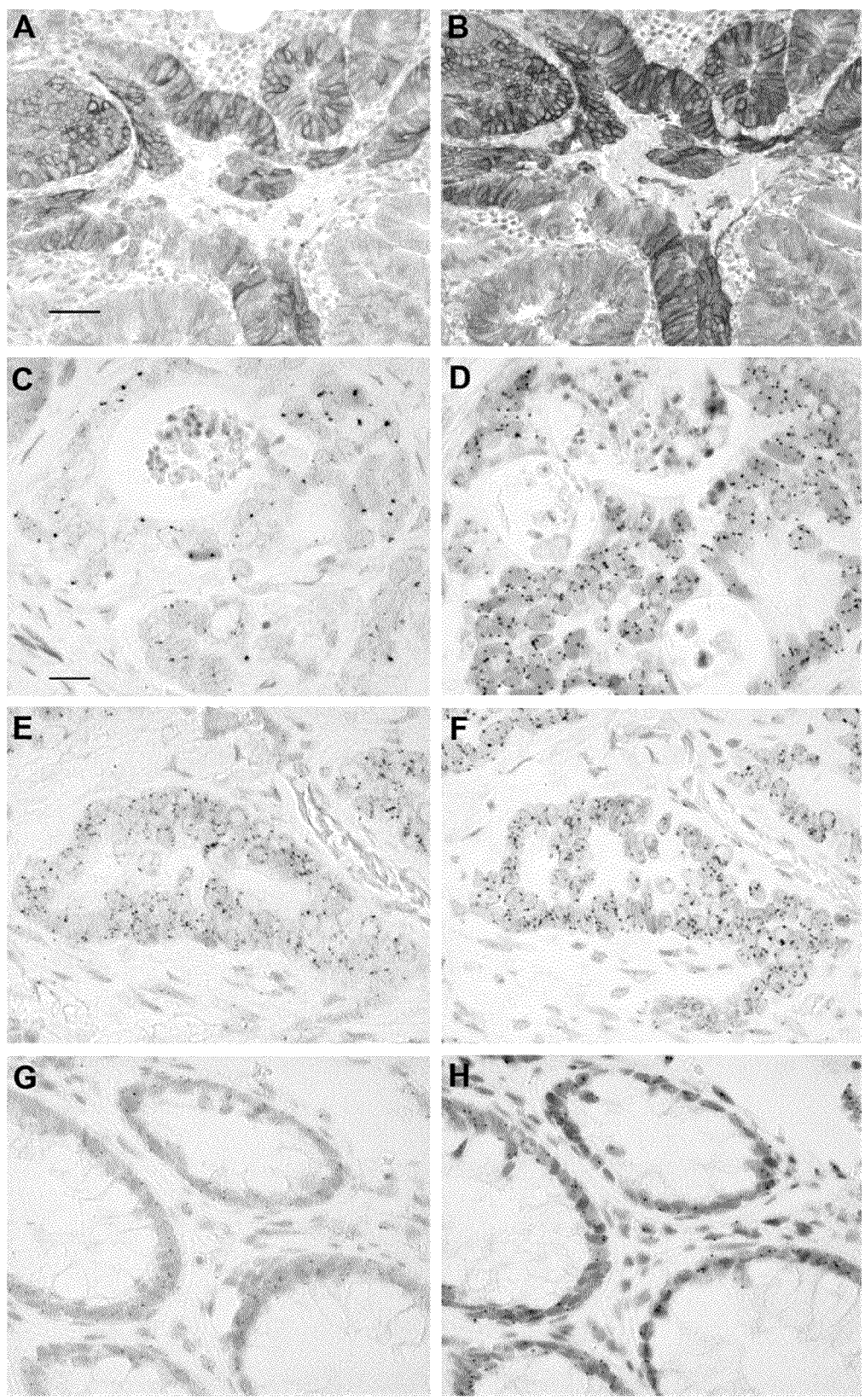
FIG. 1. The EGFR protein expression levels and EGFR SISH. EGFR IHC with clones 5B7 (A) and 3 C6. Note intratumoral variation in immunoreactivity (B). EGFR SISH revealing gene clusters (C) and the corresponding Chr-7 SISH (D). EGFR SISH with GCN≥4.0 (E) and the corresponding Chr-7 SISH (F). EGFR SISH (G) and Chr-7 SISH (H) in normal colorectal tissue. Scale bar 0.05 mm (A-B), 0.02 mm (C—H).

As used herein, the term "epidermal growth factor receptor" ("EGFR") refers to a gene that encodes a membrane polypeptide that binds, and is thereby activated by, epidermal growth factor (EGF). EGFR is also known in the literature as ERBB, ERBB1 and HER1. An exemplary EGFR is the human epidermal growth factor receptor (see Ullrich et al. (1984) Nature 309:418-425; Genbank accession number NP_005219.2; complete cds AY588246.1). Binding of an EGF ligand activates the EGFR (e.g. resulting in activation of intracellular mitogenic signaling, autophosphorylation of EGFR). One of skill in the art will appreciate that other ligands, in addition to EGF, can bind to and activate the EGFR. Examples of such ligands include, but are not limited to, amphiregulin, epiregulin, TGF-α, betacellulin, and heparin-binding EGF (HB-EGF). Intracellular domain of, a human, EGFR comprises a polypeptide sequence from amino acid adjacent to the transmembrane domain up to COOH-terminus of the EGFR. Intracellular domain comprises, inter alia, tyrosine kinase domain.

As used herein, an "EGFR gene" refers to a nucleic acid that encodes an EGFR gene product, e.g., an EGFR mRNA, an EGFR polypeptide, and the like.

As used herein, "EGFR inhibitor" refers to any agent capable of directly or indirectly inhibiting activation of an EGFR. EGFR inhibitors include agents that bind to an EGFR and inhibit its activation. EGFR inhibitors include antibodies that bind to an EGFR and inhibit activation of the EGFR; as well as small molecule tyrosine kinase inhibitors or "kinase inhibitors" that inhibit activation of an EGFR. Antibodies to EGFR include IgG; IgM; IgA; antibody fragments that retain EGFR binding capability, e.g., Fv, Fab, F(ab)$_2$, single-chain antibodies, and the like; chimeric antibodies; etc. Small molecule tyrosine kinase inhibitors of EGFR include EGFR-selective tyrosine kinase inhibitors. Small molecule tyrosine kinase inhibitors of EGFR can have a molecular weight in a range of from about 50 Da to about 10,000 Da.

The terms "k-ras" and "KRAS" as used herein are used interchangeably and refer to the KRAS gene identified as of the date of this filing in the NCBI Entrez Gene database as Accession No. NM_004985.3 (Entrez Gene database, NCBI), and/or its expression products. "KRAS" is also identified in literature as KRAS1, KRAS2, RASK2, KI-RAS, K-RAS4A, K-RAS4B or p21.

As used herein, the term "activating KRAS mutation" or "KRAS mutation is an activating mutation" refers to a mutation in a k-ras gene that results in constitutive activation of a protein encoded by k-ras, i.e. the k-ras protein activates molecules downstream in its signaling pathway in the absence of receptor bound ligand. As an example, the k-ras protein might activate downstream signaling in the absence of EGF, amphiregulin, or epiregulin binding to EGFR.

The term "tumor," as used herein, refers to any neoplastic cell growth and proliferation, whether malignant or benign, and all pre-cancerous and cancerous cells and tissues.

The terms "cancer" and "cancerous" refer to or describe the physiological condition in mammals that is typically characterized in part by unregulated cell growth. Examples of cancer include, but are not limited to, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer. In an exemplary embodiment, the cancer is colorectal cancer.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease, such as cancer, or symptom thereof and/or may be therapeutic in terms of effecting a partial or complete cure for a disease and/or symptoms of the disease. "Treatment," as used herein, covers any treatment of a disease, such as cancer, in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression or halting progression of the disease.

As used herein in the context of patient response to an EGFR inhibitor treatment, the terms "responsive", "beneficial response," "beneficial patient response," and "clinically beneficial response," "clinical benefit," and the like, are used interchangeably and refer to favorable patient response to a drug as opposed to unfavorable responses, i.e. adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment.

In a population the clinical benefit of a drug, i.e. its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

As is used herein, the term "progression free survival" refers to the time interval from treatment of the patient until the progression of cancer or death of the patient, whichever occurs first.

As used herein, the term "responder" or "responsive" refers to a patient who has an EGFR-expressing cancer, and who exhibits a beneficial clinical response following treatment with an EGFR inhibitor.

As used herein, the term "non-responder" or "non-responsive" refers to a patient who has an EGFR-expressing cancer, and who does not exhibit a beneficial clinical response following treatment with an EGFR inhibitor.

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells. The term encompasses cells that are the progeny of the patient's tumor cells, e.g. cell culture samples derived from primary tumor cells or circulating tumor cells. The term encompasses samples that may comprise protein or nucleic acid material shed from tumor cells in vivo, e.g. bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

In certain embodiments, threshold level(s) of EGFR gene copy number or level of copy number of chromosome 7 can be established, and the EGFR gene copy number or level of copy number of chromosome 7 in a patient's tumor sample can be compared to "a threshold level".

The sensitivity and specificity of a diagnostic and/or prognostic test, such as detecting and analyzing whether a patient suffering from a cancer is responsive to the treatment with an EGFR inhibitor, depends on more than just the analytical "quality" of the test, they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

In some embodiment, the ROC curve representing the patient responses to the treatment with an EGFR inhibitor may be used to define the objective function. For example, the objective function may reflect the area under the ROC curve. By maximizing the area under the curve in respect to level of EGFR gene copy number or level of copy number of chromosome 7 in patients treated with an EGFR inhibitor, one may maximize whether a patient suffering from a cancer is responsive to the treatment with an EGFR inhibitor. In some other embodiments, the ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint.

In other embodiments, other features such as use of the point at which the slope of the ROC curve is equal to one; the use of the point at which the product of sensitivity and specificity is a maximum; or combinations of two or more of these ROC-curve features may be used to define the objective function.

In some embodiments, increased levels of EGFR gene copy number or levels of copy number of chromosome 7 in the tumor sample relative to a threshold level are indicative that a patient suffering from a cancer is responsive to the treatment with an EGFR inhibitor. In some embodiments, decreased levels of EGFR gene copy number or levels of copy number of chromosome 7 in the tumor sample relative to the threshold level are indicative that a patient suffering from a cancer is non-responsive to the treatment with an EGFR inhibitor.

The term "gene copy number" is usually defined as the number of genes per genome. The term "EGFR gene copy number" means the ratio of number of EGFR genes per nucleus. In non-tumorigenic or non-neoplastic cells EGFR gene copy number is similar to or less than 2. In tissue sections of non-tumorigenic or non-neoplastic origin, GCN is similar to or less than 2, if detected with in situ hybridization.

The term "increased or amplified EGFR gene copy numbed" means that above-defined ratio in cells of a tumor correlated to a patient (who responds or is responsive to the EGFR inhibitor or anti-EGFR antibody treatment) is higher or amplified compared to the particular ratio, or threshold level, in cells of a tumor correlated to non-neoplastic cells of the same origin. Preferably, the ratio, or threshold level, (number EGFR gene/nucleus) is greater than 2 or 3 or 4 or 5 or 6 or 7. Preferably said ratio or threshold level is similar to or greater than 4, particularly if ISH is performed in 5 μm thick tissue sections. In certain embodiments the term "increased or amplified EGFR gene copy numbed" means GCN greater than the EGFR gene copy number in non-tumorigenic or non-neoplastic cells. In tissue sections thicker than 5 μm, such as 6, 7, or 8 μm, EGFR GCN, or threshold level, may be more than 4, such as 4.5, 5, 5.5, 6, 6.5 or 7 or more. In tissue sections thinner than 5 μm, e.g. 4 μm, EGFR GCN, or threshold level, may be less than 4, such as 3.5, 3, or 2.5. Preferably, the thickness of the tissue section is 3, 4, 5, 6, 7, or 8 μm or is in any range based on these values, such as 3-5 μm, 4-6 μm or 5-8 μm.

In some embodiments, EGFR gene copy number similar to or greater than 4 identifies a patient suffering from a cancer who is likely to be responsive to the treatment with an EGFR inhibitor.

According to these afore-mentioned values applicable to an "increased or amplified" EGFR gene copy number, the ratio values for a relatively decreased or lower or non-amplified copy number presented by tumor cells of patients, which do not or not effectively or positively respond, or are non-responsive, to the treatment with EGFR inhibitors or anti-EGFR antibodies are less than 2. In an embodiment said ratio, or threshold level, is less than 4. In some embodiments, EGFR gene copy number less than 4 identifies a patient suffering from a cancer and who is likely to be non-responsive to the treatment with an EGFR inhibitor.

The term "copy number of chromosome 7" means the number of chromosome 7 per nucleus. According to the invention this number is preferably similar to or greater than 4.5. In non-tumorigenic or non-neoplastic cells EGFR gene copy number is similar to or less than 2. In tissue sections of non-tumorigenic or non-neoplastic origin, GCN is similar to or less than 2, if detected with in situ hybridization.

The term "increased or amplified copy number of chromosome 7" means that above-defined ratio, or threshold level, in cells of a tumor correlated to a patient (who responds to the EGFR inhibitor or anti-EGFR antibody treatment) is higher or amplified compared to the particular ratio in cells of a tumor correlated to non-neoplastic cells of the same origin. Preferably, the ratio, or threshold level, (number of chromosome 7/nucleus) is greater than 2 or 3 or 4 or 5 or 6 or 7. Preferably said ratio, or threshold level, is similar to or greater than 4.5, particularly if ISH is performed in 5 μm thick tissue sections. In tissue sections thicker than 5 μm, such as 6, 7, or 8 µm, copy number of chromosome 7, or threshold level, may be more than 4.5, such as 5, 5.5, 6, 6.5 or 7 or more. In tissue sections thinner than 5 µm, e.g. 4 µm, copy number of chromosome 7, or threshold level, may be less than 4.5, such as 4, 3.5, 3, or 2.5. Preferably, the thickness of the tissue section is 3, 4, 5, 6, 7, or 8 µm or is in any range based on these values, such as 3-5 µm, 4-6 µm or 5-8 µm.

In some embodiments, levels of copy number of chromosome 7 similar to or greater than 4.5 identifies a patient suffering from a cancer who is likely to be responsive to the treatment with an EGFR inhibitor.

According to these afore-mentioned values applicable to an "increased or amplified" copy number of chromosome 7, the ratio values for a relatively decreased or lower or non-amplified copy number presented by tumor cells of patients, which do not or not effectively or positively respond, or are non-responsive, to the treatment with EGFR inhibitors or anti-EGFR antibodies are less than 2. In an embodiment said ratio, or threshold level, is less than 4.5. In some embodiments, levels of copy number of chromosome 7 less than 4.5 identifies a patient suffering from a cancer who is likely to be non-responsive to the treatment with an EGFR inhibitor.

Without being bound by theory, the threshold level to identify a patient suffering from a cancer who is likely to be responsive to the treatment with an EGFR inhibitor is the level of EGFR gene copy number or the level of copy number of chromosome 7 which is sufficient to divide the responsive and non-responsive patients.

A "probe" (oligonucleotide or polynucleotide or DNA probe) is a nucleic acid molecule which typically ranges in size from about 50-100 nucleotides to several hundred nucleotides to several thousand nucleotides in length. Therefore, a probe can be any suitable length for use in an assay described herein, including any length in the range of 50 to several thousand nucleotides, in whole number increments. Such a molecule is typically used to identify a target nucleic acid sequence in a sample by hybridizing to such target nucleic acid sequence under stringent hybridization conditions. Hybridization conditions have been described in detail above.

The term "enzymatic metallography" refers herein to staining methods wherein a peroxidase, such as horseradish peroxidase, can, in the presence of an metal source and activating agents, selectively deposit metal from said metal source to give a black, localized stain (see Hainfield et al., 2002, Proceedings: Microscopy and Microanalysis 2002, Cambridge University Press, New York, page 916). Preferred metals for forming these deposits are gold and silver. Enzymatic metallography is highly sensitive approach, e.g., for in situ hybridization detection.

For the purposes herein a "tissue section" of a tumor sample refers to a single part or piece of a tumor sample, e.g. a thin slice of tissue or cells cut from a tumor sample. It is understood that multiple sections of tumor samples may be taken and subjected to analysis according to the present invention. In some embodiments, the same tissue section of tumor sample is analyzed at both IHC and enzymatic metallography. In some embodiments consecutive tissue sections from tumor sample are analyzed with IHC and enzymatic metallography.

"An automated processing apparatus" means an apparatus in which IHC and/or enzymatic metallography can be performed automatically. Such apparatus may include a plurality of substrate holders, thermal control units, temperature programming, moist chamber(s), containers for liquids and buffers, etc. Exemplary automated processing apparatus include Ventana Medical Systems' DISCOVERY®XT, NexES® IHC or BENCHMARK®.

According to the present invention, an "EGFR inhibitor" is any agent that inhibits (blocks, reduces, antagonizes, decreases, reverses) the expression and/or biological activity of an epidermal growth factor receptor (EGFR), including any EGFR. Therefore, an inhibitor can include, but is not limited to, a product of drug/compound/peptide design or selection, an antibody or antigen binding fragment thereof, a protein, a peptide, a nucleic acid (including ribozymes, antisense, RNAi and aptamers), or any other agent that inhibits the expression and/or biological activity of an EGFR. For example, known inhibitors of EGFR include the drugs, gefitinib (ZD 1839, Iressa®, AstraZeneca, UK) and erlotinib (OSI 774, Tarceva®, Genentech, USA), and the monoclonal antibody, Cetuximab (Erbitux®, Imclone, Bristol-Myers Squibb). However, the invention is not limited to these specific agents, and can include an agonist (described below) of such agents or agents having substantially similar biological activity as these agents. The biological activity or biological action of a protein, such as an EGFR, refers to any function(s) exhibited or performed by a naturally occurring form of the protein as measured or observed in vivo (i.e., in the natural physiological environment of the protein) or in vitro (i.e., under laboratory conditions). Biological activities of EGFR include, but are not limited to, binding to EGF, receptor homo- or heterodimerization, tyrosine kinase activity, and downstream activities related to cellular homeostasis and development.

Tyrosine kinase inhibitors represent a class of therapeutic agents or drugs that target receptor and/or non-receptor tyrosine kinases in cells such as tumor cells. In certain instances, the tyrosine kinase inhibitor is an antibody-based (e.g., anti-tyrosine kinase monoclonal antibody, etc.) or polynucleotide-based (e.g., tyrosine kinase antisense oligonucleotide, small interfering ribonucleic acid, etc.) form of targeted therapy. Preferably, the tyrosine kinase inhibitor is a small molecule that inhibits target tyrosine kinases by binding to the ATP-binding site of the enzyme. Examples of small molecule tyrosine kinase inhibitors include, but are not limited to, gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; ST1571), dasatinib (BMS-354825), leflunomide (SU10), vandetanib (Zactima®; ZD6474), pharmaceutically acceptable salts thereof, derivatives thereof, analogs thereof, and combinations thereof. Additional examples of tyrosine kinase inhibitors suitable for use in the present invention include quinazolines (e.g., PD 153035,4-(3-chloroanilino) quinazoline, etc.), pyridopyrimidines, pyrimidopyrimidines, pyrrolopyrimidines (e.g., CGP 59326, CGP 60261, CGP 62706, etc.), pyrazolopyrimidines, 4-(phenylamino)-7H-pyrrolo[2,3-d]pyrimidines, curcumin (diferuloyl methane), 4,5-bis(4-fluoroanilino)phthalimide, tyrphostines containing nitrothiophene moieties, quinoxalines (see, e.g., U.S. Pat. No. 5,804,396), tryphostins (see, e.g., U.S. Pat. No. 5,804,396), PD0183805, PKI-166, EKB-569, IMC-1C11, Affinitac® (LY900003; ISIS 3521), and the tyrosine kinase inhibitors described in PCT Publication Nos. WO 99/09016, WO 98/43960, WO 97/38983, WO 99/06378, WO 99/06396, WO 96/30347, WO 96/33978, WO 96/33979, and WO 96/33980.

Preferred EGFR inhibitors are anti-EGFR antibodies, most preferably the anti-EGFR antibodies mentioned above and below: cetuximab, panitumumab and matuzumab in their murine, chimeric or humanized versions including their immunologically effective fragments (Fab, Fv) and immunoconjugates, especially immunocytokines.

The term "antibody" refers to an immunoglobulin molecule (or combinations thereof) that specifically binds to, or is immunologically reactive with, a particular antigen or, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), single chain Fv antibodies (scFv), polypeptides that contain at least a portion of an immunoglobulin that is sufficient to confer specific antigen binding to the polypeptide, and antigen binding fragments of antibodies, including, e.g., Fab', F(ab')$_2$, Fab, Fv, rIgG, or complementarity determining region (CDR) fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well known recombinant DNA methods. Monoclonal antibodies may also be isolated from phage antibody libraries using the techniques described in Clackson et al., Nature, 352:624-628 (1991) and Marks et al., J. Mol. Biol., 222:58, 1-597 (1991), for example.

Although the invention relates preferably to colon or colorectal cancer it is principally applicable to other cancers and tumors, which express or overexpress EGFR and occur in patients with different EGFR gene copy numbers.

Detection of KRAS

As noted above, the presence of an activating mutation in a k-ras gene (a "KRAS mutation") indicates reduced response to an EGFR inhibitor, particularly anti-EGFR antibody. The presence or absence of an activating KRAS mutation can be assayed in conjunction with assaying EGFR GCN.

Detection of an activating KRAS mutation can be carried out in conjunction with determining EGFR GCN or copy number of chromosome 7 and EGFR protein expression by immunohistochemistry, where "in conjunction with" includes in the same or different sample, and at the same time or at a different time and/or location. For example, the presence or absence of an activating KRAS mutation can be detected in a sample (e.g., a sample comprising a polynucleotide obtained from a patient's cancer cell; or a sample comprising a patient's cancer cell); and EGFR GCN or copy number of chromosome 7 can be detected in the same sample at substantially the same time and in the same location (e.g., in the same laboratory). As another example, the presence or absence of a KRAS mutation can be detected in a first sample (e.g., a sample comprising a polynucleotide obtained from a patient's cancer cell or tumor sample) at a first time; and EGFR GCN or copy number of chromosome 7 can be detected in a second sample (e.g., a tissue section of a tumor sample on a microscope slide and obtained from a patient's tumor) at a second time, where the first and second samples are assayed in the same location. As another example, the presence or absence of a KRAS mutation can be detected in a first sample (e.g., a sample comprising a polynucleotide obtained from a patient's cancer cell or tumor sample) at a first time; and EGFR GCN or copy number of chromosome 7 can be detected in a second sample (e.g., a tissue section of a tumor sample on a microscope slide and obtained from a patient's tumor) at a second time, where the first and second samples are assayed in different locations. In an embodiment, the presence of a KRAS mutation and low copy number of EGFR gene or copy number of chromosome 7 indicates a patient is not likely to responsive to therapy of an EGFR inhibitor such as panitumumab.

Alternatively, there is provided a method for detecting and analyzing whether a patient suffering from a cancer is responsive or non-responsive to the treatment with an EGFR inhibitor, the method comprising the steps of determining in a tissue section from a tumor sample obtained from said patient (i) the expression level of an EGFR protein in said tissue section by immunohistochemistry (IHC), and (ii) the level of EGFR gene copy number or the level of copy number of chromosome 7 by enzymatic metallography, wherein the area of highest expression of EGFR in a tissue section from said tumor sample is determined by IHC based on staining intensity, and said area of highest expression in the tumor sample is used in enzymatic metallography to determine gene copy number of EGFR gene or chromosome 7; and selecting said patient for treatment with said EGFR inhibitor, if the tumor sample of said patient displays expression of EGFR protein and an amplified copy number of the EGFR gene or chromosome 7. Further, the method comprises determining the presence or absence of KRAS mutation in said tumor sample whereby the presence of a wild-type KRAS protein or gene and increased copy number of EGFR gene or copy number of chromosome 7 indicates that the tumor is susceptible to treatment with an EGFR inhibitor. The presence of a mutated KRAS protein or gene and/or low copy number of EGFR gene or low copy number of chromosome 7 indicates that the tumor is not susceptible to treatment with an EGFR inhibitor or the patient is not responsive to treatment with an EGFR inhibitor. In a particular embodiment the KRAS mutation is an activating mutation.

Detection of a KRAS mutation in a tumor sample from the patient or in a sample obtained from a cancer cell from the patient involves detecting a KRAS mutation in a nucleic acid of a cancer cell present in the patient. It is possible, but not necessary, that all cancer cells in the patient comprise a KRAS mutation, e.g., a tumor can be heterogeneous with respect to KRAS mutation status. For example, the KRAS mutation may be present in less than 100%, less than 95%, less than 80%, less than 70%, less than 50%, or less than 25%, of the cancer cells present in the sample and/or in the patient. The presence of an activating KRAS mutation in any proportion of the cancer cells in the sample will indicate that the patient is not likely to be responsive to EGFR inhibitor treatment.

The presence of an activating KRAS mutation in a k-ras gene of a cancer cell is negatively correlated with a clinically beneficial response to EGFR inhibitor treatment. Exemplary activating mutations are described in, e.g., WO 2006/086777 and WO 2007/001868.

As an example, activating KRAS mutations include: 1) a G→T mutation at position 216 of a k-ras nucleotide sequence (e.g., the nucleotide sequence set forth in GenBank Accession No. NM_033360.2); 2) a G→A mutation at position 216 of a k-ras nucleotide sequence; 3) a G→C mutation at position 216 of a k-ras nucleotide sequence; 4) a G→T mutation at position 215 of a k-ras nucleotide sequence; 5) a G→A mutation at position 215 of a k-ras nucleotide sequence; 6) a G→C mutation at position 215 of a k-ras nucleotide sequence; and 7) a G→A mutation at position 219 of a k-ras nucleotide sequence.

Detection of an activating KRAS mutation can be carried out using any of a variety of methods (see below). Numerous methods are known in the art for detection of sequence variations (polymorphisms and mutations) in nucleic acid samples, and can be used for detecting an activating KRAS mutation. Such methods include methods based on de novo sequencing of nucleic acids as well as methods designed to detect sequence variants (e.g., known variants) at a targeted position in the nucleic acid sequence. Sequence variants are detected using as probes or primers oligonucleotides that hybridize differentially to each variant. Many approaches have been developed to increase the selectivity of hybridization of sequence specific probes to targeted variants; the extent of hybridization is of the sequence specific probes is often detected based on detecting and/or quantifying the amount of product formed in a subsequent polymerase chain reaction.

Detection of Chromosome 7

Suitable probes for in situ hybridization in accordance with the invention hybridize (i.e., form a duplex) with repetitive DNA associated with the centromere of a chromosome, preferably with the chromosome 7. Centromeres of human chromosomes contain a complex family of long tandem repeats of DNA, composed of a monomer repeat length of about 171 base pairs, that is referred to as alpha-satellite DNA.

Chromosomal probes are typically about 25 to about 100000 nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR).

Chromosomal probes typically are directly labeled with a fluorophore. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides.

Probes also can be indirectly labeled with biotin or digoxygenin and secondary detection molecules or further processing is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard calorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase. In a preferred embodiment the enzymatic method is an enzymatic metallography, most preferably silver in situ hybridization.

Abnormal cells are characterized by polysomy of chromosome 7 or amplified copy number of chromosome 7, as assessed by examining the hybridization pattern of the chromosomal 7 probe (e.g., the number of signals for each probe) in the cell, and recording the number of signals. In a preferred embodiment, amplified copy number of chromosome 7 or the ratio of copy number of chromosome 7, or threshold level, is greater than 4.5. For example, the cut-off, of threshold level, for amplified levels of chromosome 7 may be set at above 4.0 signals per cell and, in a preferred embodiment, the cut off, or threshold level, for amplified levels or ratio may be set at a range of about 3.5-5.5 signals per cell. However, sectioning of paraffin-embedded specimens (typically 4-6 µm) results in sectioning of cell nuclei in a manner that the number of SISH signals per cell will be somewhat lower than the actual number of copies in an intact nucleus. Therefore, thresholds for amplified levels of chromosome 7, or polysomy, and loss of copies are set empirically to reflect optimal association with response or survival. A practical cutoff, or threshold level, for amplified copy number of chromosome 7, or polysomy, may be set at about 4 CEN 7 signals per cell since this may provide a better correlation with response or survival, even though cells with 3 or 5 actual copies of CEN 7 may fall below the cutoff or threshold level. In this case, the "normal" range may include low amplification level of chromosome 7, or polysomy, and the "polysomy" range may include only higher levels of polysomy. When assessing EGFR copy number by examining the hybridization pattern of EGFR probe in a cell, the same adaptations which are described for chromosome 7 above may be applied when determining appropriate cut-offs or threshold levels.

Detection of Mutant EGFR

Mutant EGFR genes or gene products can be detected from tumor or from other body samples such as urine, sputum or serum. The same techniques discussed for detection of mutant KRAS or EGFR genes or gene products in tumor samples can be applied to other body samples when detecting mutant EGFR. Alteration of wild-type EGFR genes can also be detected by screening for alteration of wild-type EGFR protein. For example, monoclonal antibodies immunoreactive with EGFR can be used to screen a tissue. Lack of cognate antigen would indicate an EGFR mutation. Antibodies specific for products of mutant alleles could also be used to detect mutant EGFR gene product. Such immunological assays can be done in any convenient format known in the art. These include Western blots, immunohistochemical assays and ELISA assays. Any means for detecting an altered EGFR protein can be used to detect alteration of wild-type EGFR genes. Further, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR before hybridization. Changes in DNA of the EGFR gene can also be detected using Southern hybridization, especially if the changes are gross rearrangements, such as deletions and insertions. DNA sequences of the EGFR gene which have been amplified by use of polymerase chain reaction may also be screened using allele-specific probes. These probes are nucleic acid oligomers, each of which contains a region of the EGFR gene sequence harboring a known mutation. By use of a battery of allele-specific probes, PCR amplification products can be screened to identify the presence of a previously identified mutation in the EGFR gene.

Methods of Assaying a Gene Product

The methods and compositions of the present disclosure will employ, unless otherwise indicated, conventional techniques of molecular biology (including recombinant techniques), microbiology, cell biology, and biochemistry, which are within the skill of the art. Exemplary techniques are explained fully in the literature, such as, "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4.sup.th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Methods of gene expression profiling include methods based on hybridization analysis of polynucleotides, methods based on sequencing of polynucleotides, and proteomics-based methods. Exemplary methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription PCT (RT-PCR) (Weis et al., Trends in Genetics 8:263-264 (1992)). Antibodies may be employed that can recognize sequence-specific duplexes, including DNA duplexes, RNA duplexes, and DNA-RNA hybrid duplexes or DNA-protein duplexes.

Microarrays

Expression levels of a gene of interest, such as KRAS and EGFR, can also be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from mRNA of a test sample. As in the RT-PCR method, the source of mRNA typically is total RNA isolated from a tumor sample, and optionally from normal tissue of the same patient as an internal control or cell lines. mRNA can be extracted, for example, from frozen or archived paraffin-embedded and fixed (e.g. formalin-fixed) tissue samples.

Hybridization Methods

In a preferred embodiment, detection of a gene, such as EGFR or copy number of chromosome 7, is accomplished using hybridization assays. Nucleic acid hybridization simply involves contacting a probe (e.g., an oligonucleotide or larger polynucleotide) and target nucleic acid under conditions where the probe and its complementary target can form stable hybrid duplexes through complementary base pairing. As used herein, hybridization conditions refer to standard hybridization conditions under which nucleic acid molecules are used to identify similar nucleic acid molecules. Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are known for skilled artisan.

Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The hybridized nucleic acids are detected by detecting one or more labels attached to the sample nucleic acids. The labels may be incorporated by any of a number of means well known to those of skill in the art. In immunohistochemical methods same detection methods can be used as described above and below.

Many conventional detection methods utilize enzymes. The types of enzyme substrates popularly used for sensitive detection are typically colorimetric, radioactive, or fluorescent. Conventional colorimetric substrates produce a new color (or change in spectral absorption) upon enzyme action on a chromogenic substrate. This type of detection is advantageous in that the chromogens produced are easily detected by light-based microscopy or with spectral equipment. The cost of equipment for detection is also generally less than with other methods; for example in pathology, the brown color produced by the enzyme horseradish peroxidase acting on the substrate 3,3'-diaminobenzidine (DAB), requires only a simple bright field light microscope for observation of biopsied sections. Other chromogens which can be used in conjunction with horseradish peroxidase include, but are not limited to, 3-Amino-9-ethylcarbazole (AEC) and Bajoran Purple. Other chromogens which can be used in conjunction with alkaline phosphatase include, but are not limited to, Fast Red and Ferangi Blue. Numerous chromogens are available to a person having ordinary skill in the art, and are commercially available through catalogs provided by companies such as Thermo Fisher Scientific.

Various labels used in detection methods include fluorescent dyes include (e.g., fluorescein isothiocyanate, Texas red, rhodamine, and the like), and enzymes (e.g., LacZ, CAT, horseradish peroxidase, alkaline phosphatase, β-galactosidase, and glucose oxidase, acetylcholinesterase and others, commonly used as detectable enzymes), or members of a binding pair that are capable of forming complexes such as streptavidin/biotin, avidin/biotin or an antigen/antibody complex including, for example, rabbit IgG and anti-rabbit IgG; fluorophores; light scattering or plasmon resonant materials such as gold or silver particles or quantum dots; or radiolabels; and probes labeled with any other signal generating label known to those of skill in the art, as described, for example, in the $6^{th}$ Edition of the Molecular Probes Handbook by Richard P. Hoagland.

Preferably, the hybridizing nucleic acids, such as to EGFR gene and/or chromosome 7, are detected by metal labels or "enzymatic metallography" and most preferably, in the context of a silver in situ hybridization (SISH) assay. A SISH assay is described, for example, in the Examples section.

As used herein "enzymatic metallography" "or "enzymatic metallography method" is defined as a buildup or accumulation of metal (metallic elements in the zero oxidation state) in the vicinity of the enzyme. Typically, metal accumulation or deposition will start within a distance of about 1 micron from the enzyme, but deposition may start 0.005, 0.01, 0.1, 5, 10, 50, 100, 1000 microns from the enzyme. Naturally as metal deposition continues the metal accumulation may extend beyond this distance. The metal is preferably silver, gold, iron, mercury, nickel, copper, platinum, palladium, cobalt, iridium ions or mixtures thereof In a preferred embodiment, the enzymatic metallography allows deposition of silver metal in the presence of peroxidase and activating agents with high sensitivity combined with high resolution and minimal background for in situ hybridization (ISH) detection, and visualization in the conventional bright field microscope without the need for oil immersion. Such an assay is herein termed as "Silver in situ hybridization" (SISH) (see e.g. patent publication US20080299555 A1). In particular, the enzymatic metallography allows detection of a single copy of a target gene in a chromosome by a conventional bright field microscope without requiring oil immersion. SISH also enables detection of gene copies with a resolution that allows for individual enumeration of signals, such as discrete metal deposit dots for individual gene copies. In a preferred embodiment, the invention allows for detection of at least 2, 3, 4, 5, 6, 7, 8 or 9 copies of EGFR gene in human chromosome 7 in a nucleus, as discrete metal deposit dots.

The copy number of genes and chromosomes in tumor cells according to the invention can be measured, for example in SISH assays, in nuclei, and the protein expression can be evaluated, for example in immunohistochemistry assays, in tumor cell nuclei, cytoplasm and/or membranes. Both tests, e.g., SISH and immunohistochemistry, as well as other detection methods, can be performed in primary tumors, metastatic tumors, locally recurring tumors, or other tumoral settings. The tumor specimens can be fresh, frozen, fixed or otherwise preserved.

The nucleotide sequence of the human epidermal growth factor receptor (EGFR) gene is known in the art and can be found under GenBank Accession No. AY588246 (incorporated herein by reference), for example. Nucleotide probes are also known in the art and available for use as probes to detect EGFR genes. For example, such a probe for detecting both EGFR and chromosome 7 centromere sequences is available (e.g., LSI EGFR SpectrumOrange/CEP 7 SpectrumGreen probe (Vysis, Abbott Laboratories).

The patients displaying absence of KRAS mutation, or presence of wild type KRAS, and with amplified level or high EGFR gene copy numbers or a gain in copy numbers (e.g., gene amplification and/or polysomy) of EGFR, or increased levels of chromosome 7 copy number, are more likely to have a higher response rate to EGFR inhibitor therapy, a lower rate of progressive disease, a longer time to progression, and a higher rate of long term survivors. The higher the chromosome 7 polysomy or overall gain in EGFR gene copy number, the better the predicted outcome.

Immunochemical Methods

Immunochemical (also referred to herein as "immunological" or "immunohistochemical") methods are also suitable for detecting the expression levels of genes and applied to the method disclosed herein. Antibodies (e.g., monoclonal antibodies) that specifically bind a gene product of a gene of interest can be used in such methods. The antibodies can be detected by direct labeling of the antibodies themselves, for example, with radioactive labels, fluorescent labels, haptene labels such as, biotin, or an enzyme such as horse radish peroxidase or alkaline phosphatase. Alternatively, unlabeled primary antibody can be used in conjunction with a labeled secondary antibody specific for the primary antibody. Immunochemical protocols and kits are well known in the art and are commercially available. Exemplary suitable immunochemical methods include enzyme-linked immunosorbent assays, radioimmunoassays, protein blot methods (also referred to as "Western" blot methods), and enzyme immunoassays. In an embodiment, the EGFR protein in tumor sample is determined by immunohistochemistry (IHC), preferably with anti-EGFR monoclonal antibodies.

Protein Detection

In one embodiment of the present invention, the method includes a step of detecting the expression of a protein, including EGFR. Protein expression can be detected in suitable tissues, such as tumor sample or tumor cell material obtained by biopsy. For example, the patient tumor biopsy sample, which can be immobilized, can be contacted with an antibody, an antibody fragment, or an aptamer, that selectively binds to the protein to be detected, and determining whether the antibody, fragment thereof or aptamer has bound to the protein. Protein expression can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry. In a preferred embodiment, immunohistochemical (IHC) analysis is used to detect protein expression. IHC methods and preferred assessment criteria for detection of protein expression are described in detail, for example, in Hirsch et al., J. Clin. Oncol. 2003, 21:3798-3807, and are also described in the Examples.

In a preferred, but non-limiting method for assessing protein expression, the following protocol is used as an evaluation of immunohistochemistry results. EGFR expression can be scored, in one aspect of the invention, based on intensity and fraction of positive cells, although other scoring systems will be apparent to those of skill in the art, given the guidance provided herein. The intensity score can be defined as described in Examples. Statistical analyses are used to define cut-off levels, or threshold levels, to separate patients responsive and non-responsive to EGFR inhibitor treatment. It is also contemplated, for example, that this scoring system can be revised or manipulated, such as by lowering or raising the cut-off, or threshold level, score by single or multitude of scoring points.

In embodiments of the invention, tumor sample areas, or tumor cells, displaying increased levels of EGFR protein expression, as determined by IHC, are analyzed for EGFR gene copy number and/or chromosome 7 amplification. The particular object of the invention is to guide the user to aim the gene copy number counting to the area of highest EGFR protein expression in the sample. The term "highest expression" refers to the area of the sample showing highest relative IHC staining intensity in the sample. The intensity is evaluated using a four-scale semiquantitative scoring (0, 1+, 2+, 3+), where 0 represents a negative EGFR IHC result and 3+ represents a result, where staining intensity is similar to staining of the epidermal basal layer. The levels of 1+ and 2+ represent intermediate staining results between the negative staining (0) and the highest staining (3+). Thus, the performance characteristics of the present method make the visualization of four staining intensity levels possible from 0 to 3+. In the present invention, the cellular compartment wherefrom the staining intensity is determined comprises cell membrane, cytoplasm or combination of both cell membrane and cytoplasm. In this aspect, the scoring system, or evaluation of staining intensity, of the present invention differs from the interpretation of, e.g., Dako EGFR pharmDx™, which only scores tumor cell membranes (Dako EGFR pharmDx™, Interpretation Manual).

The area showing highest staining intensity may be an area with staining intensity level of 1+, 2+ or 3+ depending on the sample. The method of the invention is particularly advantageous when the IHC staining results are heterogeneous in the sample, i.e. the sample shows two or more different levels of staining. In such a case, the method guides the user to perform the following enzymatic metallography step so that the copy number of EGFR gene or chromosome 7 is counted from the area of highest EGFR protein expression (preferably 2+ or 3+) in the tumor sample. Preferably, at least 20 tumor cells are analyzed in enzymatic metallography.

The inventors have also found that a patient is more responsive to the administration of an EGFR inhibitor, if EGFR protein expression and detection of EGFR gene copy number and/or copy number of chromosome 7 are performed in the corresponding, or the same, tumor sample region or tumor cells and the results suggest that the patient would response to the treatment.

Specifically, if detection of EGFR gene copy number and/or copy number of chromosome 7 are assessed in the same tumor sample region or the same tumor cells expressing increased levels of EGFR protein (e.g. using scoring method shown in Examples), patients having tumor cells with amplified levels of EGFR copy number and/or amplified copy number of chromosome 7 had better outcomes (e.g., better response times, slower progression rates, longer survival times and were responsive) when treated with EGFR inhibitors than those patients expressing low levels of EGFR protein and low levels of EGFR gene copy number and/or low levels of copy number of chromosome 7.

KRAS mutation can be combined with detection of EGFR copy number and/or copy number of chromosome 7 with any of above protocols to improve the ability to detect patients responsive to EGFR inhibitor treatment. For example, the inventors demonstrate herein that the patients having wild type gene KRAS gene with EGFR protein expression, EGFR gene copy number amplification and/or chromosome 7 polysomy (i.e. amplified copy number of chromosome 7), are likely to be responsive to EGFR inhibitor therapy. Further, patients having a mutated KRAS gene with EGFR protein expression and low GCN of EGFR and/or low copy number of chromosome 7, are likely to be non-responsive to EGFR inhibitor therapy.

More specifically, the present inventors have demonstrated that amplified EGFR gene copy number and/or amplified copy number of chromosome 7 detected by silver in situ hybridization (SISH) and EGFR protein expression by IHC significantly correlated with response to anti-EGFR antibody therapy. Those patients carrying EGFR gene copy number amplification and/or amplified copy number of chromosome 7 and/or high EGFR protein expression in the tumor sample were responsive, i.e. had a significant improvement in response, time to progression and survival, to anti-EGFR antibody treatment. Specifically, if the assessment of EGFR gene copy number and/or copy number of chromosome 7 is detected i) in the same tumor cells or ii) in the same tumor region (e.g. in adjacent tissue slides) as EGFR protein expression. Conversely, those patients that did not demonstrate an EGFR gene copy number increase and/or chromosome 7 polysomy were refractory to anti-EGFR antibody treatment.

It will be apparent to those of skill in the art from the description of the invention herein that a variety of combinations of the above-described genes and chromosomes and detection protocols can enhance or improve the ability to identify patients that are predicted to be responsive to therapy with EGFR inhibitors (and patients that are predicted to be poor responders). Therefore, any combination of the use of the EGFR, KRAS and chromosome 7, detection protocols and detection techniques is encompassed by the invention. Moreover, the invention is not limited to the detection techniques described herein (e.g., SISH and IHC), since other techniques may be used to achieve the same result. By way of example, the following particular combinations have been demonstrated by the inventors to be particularly useful in predicting responsiveness to EGFR inhibitors: (1) detection of EGFR gene copy number and copy number of chromosome 7 using SISH; (2) combination of detection of EGFR protein expression using IHC and detection of EGFR gene copy number using SISH; (3) combination of detection of EGFR protein expression using IHC and detection of copy number of chromosome 7 using SISH; (4) combination of detection of absence or presence of mutations in the KRAS gene, and detection of EGFR protein expression using IHC and detection of EGFR gene copy number using SISH; and (5) combination of detection of absence or presence of mutations in the KRAS gene, and detection of EGFR protein expression using IHC and copy number of chromosome 7 using SISH.

Kits

An embodiment of the invention includes an assay kit for performing any of the methods of the present invention. The assay kit can include any one or more of the following components: (a) a means for determining in vitro in a tumor sample the presence or absence of a KRAS mutation; a means for detecting in a tumor sample a level of amplification of the epidermal growth factor receptor (EGFR) gene and/or a level of polysomy of the epidermal growth factor receptor (EGFR) gene; (c) a means for detecting in a tumor sample the expression of EGFR protein.

The assay kit preferably also includes one or more controls. The controls could include: (i) information containing a predetermined control for KRAS mutation; (ii) information containing a predetermined control for EGFR gene copy number; (iii) information containing level of EGFR inhibitor sensitivity or resistance (e.g., a predetermined control level of EGFR gene amplification and/or polysomy that has been correlated with sensitivity to an EGFR inhibitor or resistance to an EGFR inhibitor or EGFR immunohistochemistry).

In other embodiments, control slides upon which are mounted one or more tissue or cell preparations (e.g., xenografts, cell pellets, or clotted cells) that may serve as positive and/or negative controls for a EGFR binding molecule (e.g., monoclonal antibody (such as clone 5B7) or fragment thereof) may be provided in an appropriate and separate container. In some instances, A431, DU145, and/or Caski cells (or xenografts prepared therewith) may serve as a positive control. In other instances, MCF-7 cells (or xenografts prepared therewith) may serve as a negative control. In other embodiments, control slides upon which are mounted one or more tissue or cell preparations (e.g., xenografts, cell pellets, or clotted cells) that may serve as positive and/or negative controls for EGFR gene copy number analysis may be provided.

In one embodiment, a means for detecting KRAS mutation can generally be any type of reagent that can be used in a method of the present invention. Such a means for detecting include, but are not limited to: a probe or primer(s) that hybridizes under stringent hybridization conditions to KRAS gene. Nucleic acid sequences for the KRAS genes are known in the art and can be used to produce such reagents for detection. Additional reagents useful for performing an assay using such means for detection can also be included, such as reagents for performing in situ hybridization, reagents for performing polymerase chain reaction, etc.

In one embodiment, a means for detecting EGFR gene amplification and/or polysomy can generally be any type of reagent that can be used in a method of the present invention. Such a means for detecting include, but are not limited to: a probe or primer(s) that hybridizes under stringent hybridization conditions to an EGFR gene or a portion of chromosome 7 (chromosome on which EGFR is located). Nucleic acid sequences for the EGFR genes are known in the art and can be used to produce such reagents for detection. Additional reagents useful for performing an assay using such means for detection can also be included, such as reagents for performing in situ hybridization, reagents for detecting fluorescent markers, reagents for performing polymerase chain reaction, etc.

In another embodiment, a means for detecting EGFR protein expression can generally be any type of reagent that can be used in a method of the present invention. Such a means for detection includes, but is not limited to, antibodies and antigen binding fragments thereof, peptides, binding partners, aptamers, enzymes, and small molecules. Additional reagents useful for performing an assay using such means for detection can also be included, such as reagents for performing immunohistochemistry or another binding assay. In one embodiment of such a kit, an appropriate amount of at least one EGFR antibody (e.g., monoclonal antibody (such as clone 5B7) or fragment thereof) is provided in one or more containers.

The means for detecting of the assay kit of the present invention can be conjugated to a detectable tag or detectable label. Such a tag can be any suitable tag which allows for detection of the reagents used to detect the gene or protein of interest and includes, but is not limited to, any composition or label detectable by spectroscopic, photochemical, electrical, optical or chemical means. Useful labels and methods in the present invention include: biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads or means to perform enzymatic metallography such as SISH.

Other kit embodiments will include means for detection of the EGFR-binding molecule, such as secondary antibodies (e.g., goat anti-rabbit antibodies or rabbit anti-mouse antibodies). In some such instances, the secondary antibody will be directly labeled with a detectable moiety (as described elsewhere in this disclosure). In other instances, the primary or secondary (or higher-order) antibody will be conjugated to a hapten (such as biotin, DNP, and/or FITC), which is detectable by a detectably labeled cognate hapten-binding molecule (e.g. streptavidin (SA)-horse radish peroxidase, SA-alkaline phosphatase, and/or SA-QDot™). Some kit embodiments may include colorimetric reagents (e.g., DAB, and/or AEC) in suitable containers to be used in concert with primary or secondary (or higher-order) antibodies that are labeled with enzymes for the development of such calorimetric reagents.

In one embodiment, a kit includes instructional materials disclosing methods of use of the kit contents in a disclosed method. The instructional materials may be written, in an electronic form (e.g. computer diskette or compact disk) or may be visual (e.g. video files). The kits may also include additional components to facilitate the particular application for which the kit is designed. Thus, for example, the kits may additionally include buffers and other reagents routinely used for the practice of a particular method. Such kits and appropriate contents are well known to those of skill in the art.

The following examples are provided to illustrate certain particular features and/or embodiments. These examples should not be construed to limit the invention to the particular features or embodiments described.

EXAMPLES

Example 1

Patients and Methods

Patients and Ethics

This retrospective study comprises a series of 74 metastatic or locally advanced colorectal carcinoma patients, 49 of whom were treated with anti-EGFR therapy at the Turku University Hospital. Fifty-one percent of the patients had metastatic disease already at the time of diagnosis. The median age of the patients at diagnosis was 60 years (range, 35 to 73). Patient characteristics and treatments are presented in Table 1. The treatment response could be reliably evaluated for 44/49 (90%) of treated patients. Ten of the treated patients had a mutation in the KRAS gene due to the fact that anti-EGFR therapy was administered prior to establishment of the predictive value of KRAS testing. The response to anti-EGFR treatment was evaluated by computed tomography (CT) or magnetic resonance imaging (MRI) according to the Response Evaluation Criteria in Solid Tumors (RECIST) (Eisenhauer, 2009). The study was conducted in accordance with the Declaration of Helsinki. The clinical data were retrieved and histological samples collected and analyzed with the endorsement of the National Authority for Medico-Legal Affairs.

Example 2

KRAS Analysis

Formalin-fixed, paraffin-embedded samples with at least 30% of CRC cells were selected and analyzed for KRAS point mutations within codons 12 and 13 with the DxS K-RAS mutation kit (DxS Ltd, Manchester, UK).

Example 3

IHC

Three μm sections were stained with two monoclonal antibodies against EGFR (VentanaMedical Systems/Roche Diagnostics, Tucson Ariz.). EGFR (clone 3C6) mAB is directed against the extracellular domain of human EGFR, and EGFR mAb (clone 5B7) against the internal domain of human EGFR. Stainings were performed with BenchMark XT (Ventana/Roche) using ultraVIEW Universal DAB Detection Kit (Ventana/Roche). EGFR IHC was scored independently by three observers (OC, JS, ML) blinded of the clinical information. Three scoring parameters were recorded: the highest (covering at least 10% of tumor area), the most common staining intensity, and the localization of staining (membranous, cytoplasmic or both). Four categories of staining intensity were used: 0 (negative), + (1+, weak), ++ (2+, moderate) and +++ (3+, strong/highest, similar to intensity of basal layer of the epidermis). In cases of discordance, a consensus score was used.

Example 4

SISH

EGFR gene was detected from five μm sections with EGFR DNA Probe (Ventana/Roche) and Chromosome 7 from parallel sections with Chromosome 7 Probe (Ventana/Roche). In situ hybridizations were performed with the BenchMark XT using ultraVIEW SISH Detection Kit (Ventana/Roche). From each tumor EGFR gene copy numbers (GCN, number of copies of gene/cell) and chromosome 7 number (number of copies of chromosome/cell) were analyzed by two observers (ML, JS) from the area of highest IHC reactivity. Forty tumor cells were analyzed from the EGFR SISH slides, and 20 tumor cells from the Chr-7 SISH slides, respectively. Each tumor was assessed by the averaged number of copies of EGFR gene/cell, averaged number of copies of Chr-7/cell, and EGFR/Chr-7 copy number ratio.

The optimal cut-off values for EGFR GCN (copies/cell) and Chr-7 number were defined with the receiver operating characteristic (ROC) analysis generated on response to treatment (clinical benefit versus progressive disease) and were set at 4.0 (sensitivity 94.7%, specificity 78.6%, AUC 89.8) and 4.5 (sensitivity 84.0%, specificity 78.6%, AUC 85.2), respectively.

Example 5

FISH

FISH analysis with Vysis EGFR/CEP 7 FISH Probe Kit (Abbott Molecular Inc., USA) was performed on nine samples selected based on EGFR SISH results (3 samples with clusters, 3 samples with more than 4 copies, 3 samples with normal 2 copies), using standard protocols.

Example 6

Statistics

Statistical analyses were performed with the SAS 9.1 and Enterprise Guide 3.0 programs. Frequency table data were analyzed with the $\chi^2$-test or Fisher's exact test. Spearman correlation coefficients were calculated when correlations were analyzed. The cut-off values for EGFR GCN and Chr-7 number assessed by SISH were determined with ROC curves. Kaplan-Meier and log-rank tests were used for univariate survival analysis. When analyzing progression free survival (PFS) for the patients treated with anti-EGFR therapy (n=44) the survival time was calculated from the onset of anti-EGFR treatment until disease progression. When evaluating the overall survival (OS) the survival time was calculated from the onset of anti-EGFR therapy until death.

Multivariate survival analysis was carried out by using Cox's proportional hazards model. All statistical tests were two-sided. P-values<0.05 were considered to be statistically significant.

Example 7

Results

The EGFR protein expression levels and subcellular localizations were examined by two different anti-EGFR antibodies: clone 5B7 and clone 3C6. In general, the intensity and subcellular localization of IHC reactivity showed considerable intratumoral variation with both antibodies (FIG. 1). Therefore, the following parameters were determined: localization, highest and most common intensity. The results obtained with the two different antibodies statistically significantly correlated with each other disregarding the parameter used (p<0.0001, Spearman). The most intense areas were scored as moderate (++ or 2+) in a majority of the tumors, while only one tenth of the tumors showed areas of strong intensity (+++ or 3+). The most common EGFR staining intensity was low (+ or 1+) with both antibodies. The frequencies of each staining intensity (the highest and the most common) and their subcellular localizations are presented in Table 2.

The mean EGFR GCN was 5.6 (median 5.7) and the mean Chr-7 number 5.4 (median 5.5). Forty-six tumors (65%) had an EGFR GCN above cut-off value (≥4.0) and 25 tumors (35%) were below the cut-off value. The EGFR GCN analysis by SISH could not be performed in 3/74 (4%) of the cases due to technical problems. Chr-7 number was ≥4.5 in 46/74 (62%) of the tumors, the remaining 28 (38%) were <4.5. The highest EGFR/Chr-7 gene copy number ratio was 1.7 (mean 1.0, median 1.0), The FISH results from nine selected tumors correlated with the SISH results.

An increased EGFR GCN and Chr-7 number correlated positively with EGFR IHC analyzed by 5B7 antibody (Spearman, p=0.01 for both) (Table 3). The correlation remained statistically significant when the staining intensity (IHC) was dichotomized into categories 0 and + (1+) vs. ++ (2+) and +++ (3+). A statistically significant correlation between 3C6 reactivity and an increased Chr-7 number was seen (Spearman, p=0.04), whereas, no correlation was observed between 3C6 reactivity and EGFR GCN. The subcellular localization of the EGFR IHC (5B7 and 3C6 antibodies) did not correlate with EGFR GCN or the Chr-7 number. KRAS mutational status did not correlate either with EGFR and Chr-7 SISH or EGFR IHC results.

Figure 2:
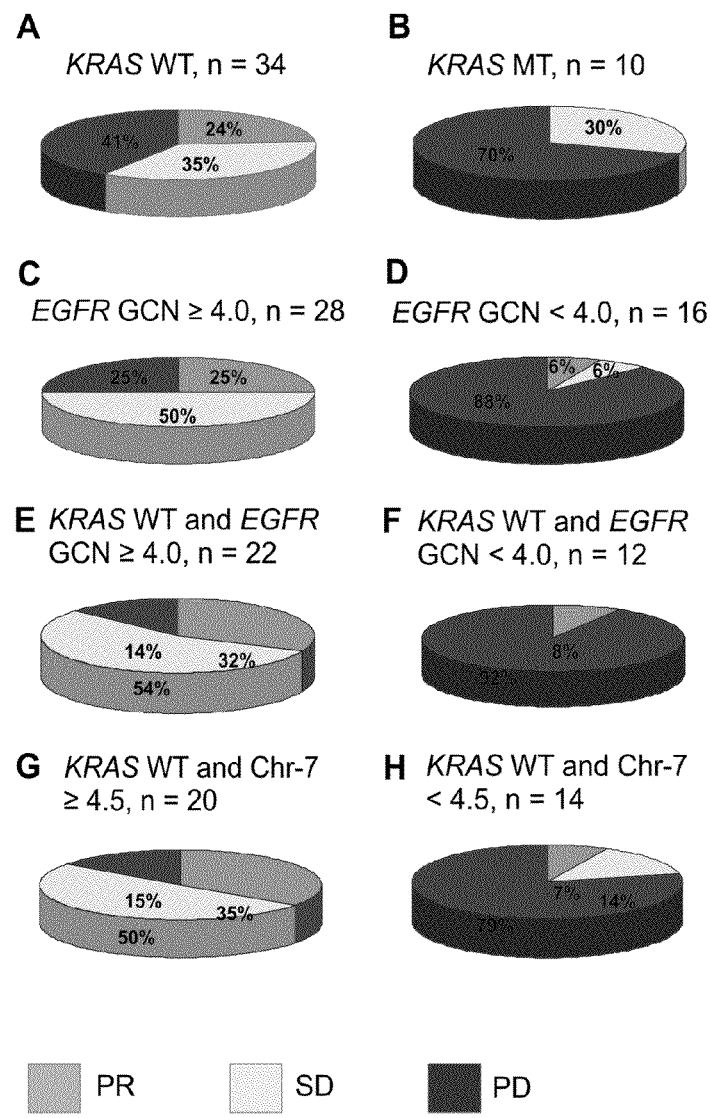
FIG. 2. Tumor response of patients with KRAS mutational status, EGFR GCN and level of copy number of chromosome 7. PR=partial response, SD=stable disease, PD=progressive disease.
Figure 3:
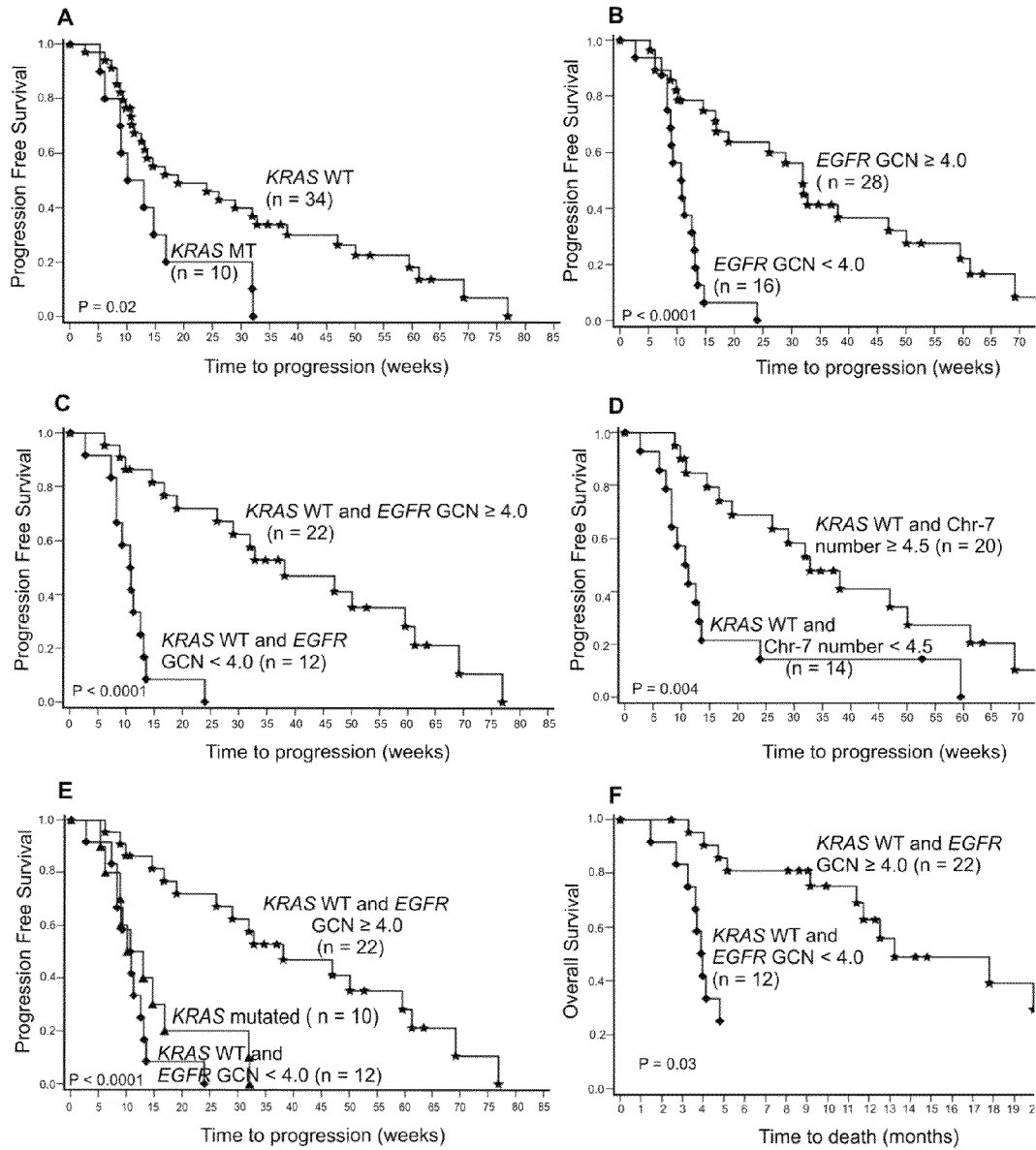
FIG. 3. Kaplan Meier diagrams of patients with KRAS mutational status, EGFR GCN and level of copy number of chromosome 7. Progression-free survival (PFS) in anti-EGFR treated patients by (A) KRAS mutation status and (B) EGFR GCN. PFS in KRAS WT patients according to EGFR GCN (C) and Chromosome 7 (Chr-7) number (D). (E) Comparison of PFS of patients with KRAS WT/EGFR GCN is ≥4.0, KRAS WT/EGFR GCN<4.0 and KRAS MUT. (F) OS in KRAS WT patients according to EGFR GCN.

An objective response (complete response (CR)+partial response (PR)) to anti-EGFR therapy was achieved in 24% and clinical benefit (CR+PR+stable disease (SD)) in 59% of the KRAS WT patients (FIG. 2A). The median duration of the response was 17.8 weeks (FIG. 3). In the group of KRAS mutated (MT) patients no objective responses were seen, three patients had a SD (FIG. 2B). Only 25% of the patients with a high EGFR GCN (≥4.0) did not respond (PD) to anti-EGFR therapy (FIG. 2C), whereas a majority of the patients (88%) with a low EGFR GCN were non-responders (FIG. 2D). In comparison, 41% (14/34) of the KRAS WT patients did not respond to treatment (FIG. 2A). In KRAS WT patients with a high EGFR GCN (≥4.0) the objective response rate was higher (32%, 7/22) and clinical benefit was more often observed (86%) (FIG. 2E) than in the overall KRAS WT population (FIG. 2A). The median PFS time almost doubled to 34 weeks (FIG. 3). In contrast, for those KRAS WT patients with a low EGFR GCN (<4.0) the median duration of response was only 11 weeks and an objective response was achieved in only one patient (8%) (FIG. 2F). The PFS time of the KRAS WT patients with an EGFR GCN below 4.0 was similar to those with mutated KRAS and the majority of those patients (92%) did not respond at all to anti-EGFR therapy (FIGS. 2F and 3). A high Chr-7 number (≥4.5) was also statistically significantly associated with an improved anti-EGFR treatment response in KRAS WT patients (FIG. 2G).

Anti-EGFR drugs were given as first line treatment to five KRAS WT patients, four of which (80%) showed an objective response. Interestingly, all four patients had an EGFR GCN≥4.0. The fifth KRAS WT patient had an EGFR GCN below 4.0 and progressed during therapy. Therefore, we performed the statistical analyses separately by excluding the five KRAS WT patients who received anti-EGFR therapy as first line treatment. Improved response rates were still seen in the group of KRAS WT patients with a high EGFR GCN (≥4.0); an objective response was observed in 17% (3/18), stable disease in 67% (12/18) and progressive disease in 17% (3/18) of the patients. In the patients with a low EGFR GCN (<4.0), PD was seen in 91% (10/11) of the cases (Fischer's Exact Test, p=0.00009).

In the entire treated population, the EGFR GCN and Chr-7 number associated significantly with an improved PFS, both when using the ROC-curve based cut-off value of 4.0 (Table 4). Significantly increased PFS was also seen within KRAS WT patients, but not among KRAS MT patients. Interestingly, the PFS of the KRAS WT patients with EGFR GCN<4.0 was indifferent from those with KRAS mutation. The median PFS time of KRAS WT/EGFR GCN ≥4.0 was 34 weeks compared to only 11 weeks of the KRAS WT/EGFR GCN<4.0 patients. Similarly, KRAS WT patients with high Chr-7 number (≥4.5) had a longer median PFS time than the ones with a low Chr-7 number; 32 weeks vs. 11 weeks. The PFS remained statistically significantly longer in the KRAS WT patient population with a high EGFR GCN when analyzing only the patients treated with anti-EGFR therapy in second line or more (Log-Rank test, p<0.0001). The responses, PFS and OS times and p-values are summarized in Table 4.

Other factors associated with improved PFS in the entire group of anti-EGFR treated patients were tumor differentiation grade (Log-Rank Test, p=0.008) and the absence of KRAS gene mutation (Log-Rank test, p=0.03).

The EGFR GCN≥4.0 associated statistically significantly with improved OS (Log-Rank test, p=0.02) in the entire treated population and in the subgroup of KRAS WT patients (Log-Rank test, p=0.03). Among KRAS MT patients no such association was found. The Chr-7 number did not associate with OS. The median OS time for patients with KRAS WT/EGFR GCN≥4.0 tumors was 50 weeks compared to 17 weeks for those with KRAS WT/EGFR GCN below the cut-off value. Longer median OS time was also observed among KRAS WT patients with Chr-7 number above the cut-off value compared to the patients with a low Chr-7 number; 46 vs. 19 weeks. When excluding the patients treated with anti-EGFR therapy in first line the OS was still significantly higher in those patients with an EGFR GCN≥4.0 (Log Rank Test, p=0.001).

P-values were calculated with the Cox's multivariate analysis method for variables that in univariate survival analysis significantly associated with PFS and OS in the anti-EGFR treated patient group. The multivariate analysis for PFS included EGFR GCN, Chr-7 number, tumor differentiation grade and KRAS status. EGFR GCN (p=0.01, HR 0.11, 95% CI 0.02-0.62) and tumor differentiation grade (p=0.01, HR 0.48, 95% CI 0.26-0.83) proved to be independent predictors of PFS, whereas no statistically significant predictive value was observed for KRAS gene status (p=0.09, HR 0.48, 95% CI 0.26-0.83). When the KRAS WT patients were analyzed separately, EGFR GCN (p=0.007, HR 0.06, 95% CI 0.008-0.45) and tumor differentiation grade (p=0.046, HR 0.45, 95% CI 0.22-1.0) independently predicted PFS.

Methodological difficulties as well as reproducibility concerns have until now prevented the usage of EGFR GCN as a predictive marker in the clinic. The fully automated SISH technique, e.g. with and automated processing apparatus, offers several advantages compared to manually performed FISH and CISH. Automation improves reproducibility and compared to FISH, SISH enables morphological identification of the analyzed tissue, which facilitates the interpretation.

For many years, there have been unsuccessful attempts to use EGFR IHC as a predictor of response to EGFR-targeted therapies (Cappuzzo, 2008; Martin, 2009). In addition, the correlation between EGFR IHC and EGFR GCN has been poor (Frattini, 2007; Spindler, 2006; Shia, 2005). Many reasons have been proposed to explain this, like storage time of tumour tissue, the choice of primary antibody and the lack of standardised criteria for evaluation (Martin, 2009). The anti-EGFR (clone 5B7) antibody of the current study, directed against the internal domain of human EGFR showed a statistically significant correlation with the EGFR GCN and Chr-7 number. Also the anti-EGFR (clone 3C6) directed against the extracellular domain of human EGFR, showed a statistically significant correlation with Chr-7. To our knowledge, there is no evidence of such a good correlation between EGFR IHC and EGFR GCN/Chr-7 number in previous publications. The 5B7 antibody detects the functionally active intracellular domain of EGFR, whereas all other commercially available antibodies bind to the external domain of the EGFR. However, the aspect that the IHC scoring method may play a role, the highest intensity assessment providing the best correlation with EGFR GCN. Typically, IHC showed a constant intensive membranous staining in the corresponding area where EGFR amplification was found. Consequently, although IHC does not predict treatment response, it is useful for guiding SISH analysis, i.e. indicating tumor areas with highest degree of EGFR GCN. Therefore, the present method is particularly useful with EGFR protein expressing cancer samples which have heterogeneous EGFR IHC staining pattern.

Of note, we observed a high EGFR GCN (≥4.0) in combination with a weak (+) EGFR protein immunoreactivity (IHC, 5B7 antibody) in 7/44 (15.9%) of the anti-EGFR treated patients. Clinical benefit was achieved for all these patients; of whom 57.1% had a partial response. The one KRAS mutant patient among these had a SD response to treatment. These findings are contradictory to the detection of HER-2 amplification in breast cancer, in which negative (−) and low (+) HER-2 protein expression (IHC) indicates low GCN and precludes further analyzed by in situ hybridization.

Currently, patients with advanced CRC are screened for KRAS status and only treat the patients with KRAS WT tumors with anti-EGFR therapy. This selection is not absolute and about half of the patients with KRAS WT tumors will end up receiving the anti-EGFR monoclonal antibodies unnecessarily. Although a BRAF mutation may explain a small fraction of unresponsiveness (Engstrom, 2009), the search for further predictive markers is feasible. Improved predictive testing would reduce the healthcare costs and at the same time minimize the risk of exposing the patients to harmful side-effects caused by EGFR targeted therapies. Our results suggest, that cetuximab and panitumumab should not be offered to KRAS WT patients with EGFR GCN below 4.0 or Chr-7 number below 4.5.

Example 8

Head and Neck Cancer Study Outline

Head and neck cancer cells often express EGFR, and its presence is associated with a poor outcome. Anti-EGFR antibody treatment is effective in recurrent or metastatic squamous-cell carcinoma of the head and neck that progresses despite platinum-containing therapy (Vermorken et al. 2007; Baselga et al. 2005).

In first-line therapy, adding cetuximab cytotoxic agents improves the response rate as compared with cytotoxic agents alone (Burtness et al. 2005; Bourhis et al. 2006).

A recent study could not identify markers that would predict response to-anti-EGFR antibody treatment (Khambata-Ford et al. 2010).

To demonstrate the usefulness of the present invention for head and neck cancer a retrospective study is performed with a series of e.g. 70-100 head and neck cancer patients who have been treated with anti-EGFR therapy or in any clinical setting described in the above references. The treatment response of treated patients is evaluated. KRAS gene mutation analysis, EGFR gene mutation analysis, anti-EGFR protein IHC and scoring of EGFR protein levels, SISH, and statistics are performed as described in the above Examples.

Example 9

Lung Cancer Study Outline

In NSCLC, EGFR receptor signalling is often activated, either due to activating mutations or overexpression of EGFR, and therefore some patients benefit from treatment anti-EGFR antibodies or anti-EGFR small molecule compounds. The methods for predicting response to anti-EGFR therapy need to be established (Coate et al. 2009).

To demonstrate the usefulness of the present invention for head and neck cancer a retrospective study is performed with a series of e.g. 70-100 lung cancer patients who have been treated with anti-EGFR therapy or in line with clinical setting described above. The treatment response of treated patients is evaluated. KRAS gene mutation analysis, EGFR gene mutation analysis, anti-EGFR protein IHC and scoring of EGFR protein levels, SISH, and statistics are performed as described in the above Examples.

Example 10

Glioma Study Outline

EGFR is over expressed in 40%-60% of glioblastoma multiforme and EGFR gene amplification is frequently associated with a mutant EGFR called variant 3 (EGFRvIII) in which deletion of exons 2-7 generates a constitutively active receptor, even in the absence of ligand-binding (Nishikawa et al. 1994). There are ongoing trials to evaluate the value of anti-EGFR treatment in recurring gliomas and glioblastoma multiforme.

To demonstrate the usefulness of the present invention for head and neck cancer a retrospective study is performed with a series of e.g. 70-100 glioma patients who have been treated with anti-EGFR therapy. The treatment response of treated patients is evaluated. KRAS gene mutation analysis, EGFR gene mutation analysis, anti-EGFR protein IHC and scoring of EGFR protein levels, SISH, and statistics are performed as described in the above Examples.

REFERENCES

Allegra C J, Jessup J M, Somerfield M R, et al: American Society of Clinical Oncology provisional clinical opinion: testing for KRAS gene mutations in patients with metastatic colorectal carcinoma to predict response to anti-epidermal growth factor receptor monoclonal antibody therapy. J Clin Oncol 27:2091-2096, 2009

Baselga J, Trigo J M, Bourhis J, et al. Phase 11 multicenter study of the antiepidermal growth factor receptor monoclonal antibody cetuximab in combination with platinum-based chemotherapy in patients with platinum-refractory metastatic and/or recurrent squamous cell carcinoma of the head and neck. J Clin Oncol 2005; 23:5568-5577

Bokemeyer C, Bondarenko I, Makhson A, et al: Fluorouracil, leucovorin, and oxaliplatin with and without cetuximab in the first-line treatment of metastatic colorectal cancer. J Clin Oncol 27:663-671, 2009

Bourhis J, Rivera F, Mesia R, et al. Phase I/II study of cetuximab in combination with cisplatin or carboplatin and fluorouracil in patients with recurrent or metastatic squamous cell carcinoma of the head and neck. J Clin Oncol 2006; 24:2866-2872

Burtness B, Goldwasser M A, Flood W, Mattar B, Forastiere A A. Phase III randomized trial of cisplatin plus placebo compared with cisplatin plus cetuximab in metastatic/recurrent head and neck cancer: an Eastern Cooperative Oncology Group study. J Clin Oncol 2005; 23:8646-8654

Cappuzzo F, Finocchiaro G, Rossi E, et al: EGFR FISH assay predicts for response to cetuximab in chemotherapy refractory colorectal cancer patients. Ann Oncol 19:717-723, 2008

Chung K Y, Shia J, Kemeny N E, et al: Cetuximab shows activity in colorectal cancer patients with tumors that do not express the epidermal growth factor receptor by immunohistochemistry. J Clin Oncol 23:1803-1810, 2005

Coate L E, John T, Tsao M-S, Shepherd F A. Molecular predictive and prognostic markers in non-small-cell lung cancer, Lancet Oncol 10:1001-1010, 2009

Cunningham D, Humblet Y, Siena S, et al: Cetuximab monotherapy and cetuximab plus irinotecan in irinotecan-refractory metastatic colorectal cancer. N Engl J Med 351:337-345, 2004

Eisenhauer E A, Therasse P, Bogaerts J, et al: New response evaluation criteria in solid tumours: revised RECIST guideline (version 1.1). Eur J Cancer 45:228-247, 2009

Engstrom P F, Arnoletti J P, Benson A B, 3rd, et al: NCCN Clinical Practice Guidelines in Oncology: colon cancer. J Natl Compr Canc Netw 7:778-831, 2009

Frattini M, Saletti P, Romagnani E, et al: PTEN loss of expression predicts cetuximab efficacy in metastatic colorectal cancer patients. Br J Cancer 97:1139-1145, 2007

Gaiser T, Waha A, Moessler F, Bruckner T, Pietsch T, von Deimling A. Comparison of automated silver enhanced in situ hybridization and fluorescence in situ hybridization for evaluation of epidermal growth factor receptor status in human glioblastomas. Mod Pathol 2009; 22:1263-1271.

Hanawa M, Suzuki S, Dobashi Y, Yamane T, Kono K, Enomoto N, Ooi A. EGFR protein overexpression and gene amplification in squamous cell carcinomas of the esophagus. Int J Cancer 2006; 118:1173-1180.

Hemmings C, Broomfield A, Bean E, Whitehead M, Yip D Immunohistochemical expression of EGFR in colorectal carcinoma correlates with high but not low level gene amplification, as demonstrated by CISH. Pathology 2009; 41:356-360.

Khambata-Ford S, Harbison C T, Hart L L, Awad M, Xu L-A, Horak C E, Dakhil S, Hermann R C, Lynch T J, Weber M R. Analysis of Potential Predictive Markers of Cetuximab Benefit in BMS099, a Phase III Study of Cetuximab and First-Line Taxane/Carboplatin in Advanced Non-Small-Cell Lung Cancer J. Clin. Oncol., 28. 918-927, 2010

Laurent-Puig P, Cayre A, Manceau G, et al: Analysis of PTEN, BRAF, and EGFR Status in Determining Benefit From Cetuximab Therapy in Wild-Type KRAS Metastatic Colon Cancer. J Clin Oncol 2009

Lievre A, Bachet J B, Le Corre D, et al: KRAS mutation status is predictive of response to cetuximab therapy in colorectal cancer. Cancer Res 66:3992-3995, 2006

Linardou H, Dahabreh I J, Kanaloupiti D, et al: Assessment of somatic k-RAS mutations as a mechanism associated with resistance to EGFR-targeted agents: a systematic review and meta-analysis of studies in advanced non-small-cell lung cancer and metastatic colorectal cancer. Lancet Oncol 9:962-972, 2008

Martin V, Mazzucchelli L, and Frattini M: An overview of the epidermal growth factor receptor fluorescence in situ hybridisation challenge in tumour pathology. J Clin Pathol 62:314-324, 2009

Miyanaga T, Hirato J, Nakazato Y. Amplification of the epidermal growth factor receptor gene in glioblastoma: an analysis of the relationship between genotype and phenotype by CISH method. Neuropathology 2008; 28:116-126.

Moroni M, Veronese S, Benvenuti S, et al: Gene copy number for epidermal growth factor receptor (EGFR) and clinical response to antiEGFR treatment in colorectal cancer: a cohort study. Lancet Oncol 6:279-286, 2005

Nishikawa R, Ji X D, Harmon R C, et al. A mutant epidermal growth factor receptor common in human glioma confers enhanced tumorigenicity. Proc Natl Acad Sci USA. 91:7727-7731, 1994

Personeni N, Fieuws S, Piessevaux H, et al: Clinical usefulness of EGFR gene copy number as a predictive marker in colorectal cancer patients treated with cetuximab: a fluorescent in situ hybridization study. Clin Cancer Res 14:5869-5876, 2008

Saltz L B, Meropol N J, Loehrer P J, Sr., et al: Phase II trial of cetuximab in patients with refractory colorectal cancer that expresses the epidermal growth factor receptor. J Clin Oncol 22:1201-1208, 2004

Sartore-Bianchi A, Moroni M, Veronese S, et al: Epidermal growth factor receptor gene copy number and clinical outcome of metastatic colorectal cancer treated with panitumumab. J Clin Oncol 25:3238-3245, 2007

Scartozzi M, Bearzi I, Mandolesi A, et al: Epidermal Growth Factor Receptor (EGFR) gene copy number (GCN) correlates with clinical activity of irinotecan-cetuximab in K-RAS wild-type colorectal cancer: a fluorescence in situ (FISH) and chromogenic in situ hybridization (CISH) analysis. BMC Cancer 9:303, 2009

Shia J, Klimstra D S, Li A R, et al: Epidermal growth factor receptor expression and gene amplification in colorectal carcinoma: an immunohistochemical and chromogenic in situ hybridization study. Mod Pathol 18:1350-1356, 2005

Sholl L M, Yeap B Y, Iafrate A J, et al. Lung adenocarcinoma with EGFR amplification has distinct clinicopathologic and molecular features in never-smokers. Cancer Res 2009; 69:8341-8348.

Siena S, Sartore-Bianchi A, Di Nicolantonio F, et al: Biomarkers predicting clinical outcome of epidermal growth factor receptor-targeted therapy in metastatic colorectal cancer. J Natl Cancer Inst 101:1308-1324, 2009

Spindler K L, Lindebjerg J, Nielsen J N, et al: Epidermal growth factor receptor analyses in colorectal cancer: a comparison of methods. Int J Oncol 29:1159-1165, 2006

Van Cutsem E, Kohne C H, Hitre E, et al: Cetuximab and chemotherapy as initial treatment for metastatic colorectal cancer. N Engl J Med 360:1408-1417, 2009

Vermorken J B, Trigo J, Hitt R, et al. Open-label, uncontrolled, multicenter phase II study to evaluate the efficacy and toxicity of cetuximab as a single agent in patients with recurrent and/or metastatic squamous cell carcinoma of the head and neck who failed to respond to platinum-based therapy. J Clin Oncol 2007; 25:2171-2177

TABLE 1

Baseline characteristics of patients who underwent SISH for EGFR and Chromosome 7 and analysis of KRAS gene mutational status (A) and the subgroup of these patients that received anti-EGFR therapy with evaluable treatment response and sufficient follow up data (B).

|  | A. Eligible patients for KRAS mutational status analysis, EGFR and Chromosome 7 SISH analysis (n = 74) | B. Patients treated with anti-EGFR therapy (n = 44) | |
|---|---|---|---|
|  | KRAS WT and MT, n = 74 n (%) | KRAS WT, n = 34 n (%) | KRAS MT, n = 10 n (%) |
| Sex | | | |
| Female | 32 (43.2) | 16 (47.1) | 6 (60) |
| Male | 42 (56.8) | 18 (52.9) | 4 (40) |
| Site of primary tumor | | | |
| Colon | 47 (63.5) | 23 (67.7) | 6 (60) |
| Rectum | 26 (35.1) | 11 (32.3) | 4 (40) |
| Unknown | 1 (1.4) | | |
| Metastatic sites | | | |
| Single | 26 (35.1) | 12 (35.3) | 1 (10) |
| Multiple | 48 (64.9) | 22 (64.7) | 9 (90) |
| Tumor differentiation grade | | | |
| Grade 1 | 10 (13.5) | 5 (14.7) | 1 (10) |
| Grade 2 | 47 (63.5) | 22 (64.7) | 6 (60) |
| Grade 3 | 12 (16.2) | 5 (14.7) | 2 (20) |
| Unknown | 5 (6.8) | 2 (5.9) | 1 (10) |
| Follow up data of the patients | | | |
| Alive with disease | 29 (39.2) | 11 (32.4) | — |
| Alive and free of disease | 5 (6.8) | — | — |
| Died of disease | 40 (54) | 23 (67.6) | 10 (100) |
| KRAS mutational status | | | |
| KRAS wild type | 49 (66.2) | 34 (100) | — |
| KRAS mutated | 23 (31.1) | — | 10 (100) |
| Not evaluable | 2 (2.7) | — | — |
| Anti-EGFR treatment | | | |
| Cetuximab | 44 (59.4) | 30 (88.2) | 10 (100) |
| Panitumumab | 4 (5.4) | 3 (8.8) | — |
| Both | 1 (1.4) | 1 (3.3) | — |
| None | 25 (33.8) | — | — |
| Line of therapy | | | |
| First | 7 (14.3) | 5 (14.7) | 1 (10) |
| Second | 11 (22.4) | 9 (26.5) | — |
| Third or more | 31 (63.3) | 20 (58.8) | 9 (90) |
| Anti-EGFR combination therapy | | | |
| Anti-EGFR combined to IRI | 33 (67.3) | 22 (64.7) | 9 (90) |
| Anti-EGFR combined to OXA | 10 (20.4) | 8 (23.6) | 1 (10) |

TABLE 1-continued

Baseline characteristics of patients who underwent SISH for EGFR and Chromosome 7 and analysis of KRAS gene mutational status (A) and the subgroup of these patients that received anti-EGFR therapy with evaluable treatment response and sufficient follow up data (B).

|  | A. Eligible patients for KRAS mutational status analysis, EGFR and Chromosome 7 SISH analysis (n = 74) | B. Patients treated with anti-EGFR therapy (n = 44) | |
|---|---|---|---|
|  | KRAS WT and MT, n = 74 n (%) | KRAS WT, n = 34 n (%) | KRAS MT, n = 10 n (%) |
| Anti-EGFR combined to CAP | 2 (4.1) | 1 (2.9) | — |
| Single treatment | 4 (8.2) | 3 (8.8) | — |

Abbreviations:
SISH, silver in situ hybridization;
EGFR, epidermal growth factor receptor;
WT, wild type;
MT, mutated;
IRI, irinotecan;
OXA, oxaliplatin;
CAP, capecitabine

TABLE 2

EGFR protein expression assessed by anti-EGFR clone 5B7 and anti-EGFR clone 3C6 antibodies (n = 74).

|  | 5B7 (H) | 5B7 (C) | 3C6 (H) | 3C6 (C) |
|---|---|---|---|---|
|  | n (%) | | | |
| Intensity | | | | |
| Negative | 0 (0) | 11 (14.9) | 9 (12.2) | 31 (41.9) |
| 1+ | 18 (24.3) | 45 (60.8) | 20 (27.0) | 37 (50.0) |
| 2+ | 48 (64.9) | 18 (24.3) | 38 (51.3) | 6 (8.1) |
| 3+ | 8 (10.8) | 0 (0) | 7 (9.5) | 0 (0) |
| Localization | | | | |
| Membranous | 23 (31.1) | 11 (14.9) | 24 (32.4) | 11 (14.9) |
| Cytoplasmic | 22 (29.7) | 40 (54.0) | 18 (24.3) | 28 (37.8) |
| Both | 29 (39.2) | 12 (16.2) | 23 (31.1) | 4 (5.4) |
| Negative | 0 (0) | 11 (14.9) | 9 (12.2) | 31 (41.9) |

H = highest staining,
C = most common staining

TABLE 3

Correlations of EGFR GCN (SISH), Chr-7 number (SISH), KRAS status and EGFR protein expression (IHC), n = 74 (p-values, Spearman.

|  | KRAS status | EGFR GCN (SISH) Continuos variable | Chr-7 (SISH) Continuos variable |
|---|---|---|---|
| anti-EGFR clone 5B7, intensity | | | |
| Highest† | ns | 0.01* | 0.01* |
| Most common† | ns | ns | ns |
| Positive or negative‡ | ns | 0.01* | 0.04* |
| anti-EGFR clone 3C6, intensity | | | |
| Highest† | ns | ns | 0.04* |
| Most common† | ns | ns | ns |
| Positive or negative‡ | ns | ns | ns |
| Localization | | | |
| 5B7§ | ns | ns | ns |
| 3C6§ | ns | ns | ns |
| EGFR GCN (SISH) | | | |
| Continuous variable | ns | — | <0.0001* |
| Cut-off 4.0 | ns | — | — |
| Cut-off 2.92 | ns | — | — |
| Chr-7 number (SISH) | | | |
| Continuous variable | ns | <0.0001* | — |
| Cut-off 4.5 | ns | — | — |
| Cut-off 2.92 | ns | — | — |

Abbreviations:
EGFR, epidermal growth factor receptor;
GCN, gene copy number;
Chr-7, chromosome 7;
IHC, immunohistochemistry;
ns, not significant;
SISH, silver in situ hybridization;
*significant p-value;
†0, 1+, 2+ or 3+;
‡positive = 2+ or 3+, negative = 0 or 1+;
§membranous, cytoplasmic, both cytoplasmic and membranous or negative

TABLE 4

Tumor response of patients with KRAS wild type (n = 34) and KRAS mutated (n = 10) metastatic or locally advanced colorectal cancer treated with anti-EGFR therapy according to different cut-off values of EGFR Gene Copy Number and Chromosome 7 number Evaluated by SISH

|  | Total No. of patients | PR | SD | PD | p-value Fisher's Exact Test | PFS time median (days) | p-value Log-Rank Test (PFS) | HR | 95% CI | OS time median (days) | p-value Log-Rank Test (OS) | HR | 95% CI |
|---|---|---|---|---|---|---|---|---|---|---|---|---|---|
| KRAS WT and MT | 44 | | | | | | | | | | | | |
| All KRAS WT patients | 34 | 8 (23.5) | 12 (35.3) | 14 (41.2) | ns | 125 | 0.02 | 0.43 | 0.20-0.91 | 273.5 | 0.3 | 0.71 | 0.33-1.43 |
| All KRAS MT patients | 10 | 0 | 3 (30) | 7 (70) | | 81 | | | | 249 | | | |
| EGFR GCN ≥4.0 | 28 | 7 (25.0) | 14 (50) | 7 (25.0) | 0.0003 | 224 | <0.0001 | 0.16 | 0.07-0.37 | 355 | 0.05 | 0.49 | 0.24-1.02 |
| EGFR GCN <4.0 KRAS WT | 16 | 1 (6.25) | 1 (6.25) | 14 (87.5) | | 75.5 | | | | 121.5 | | | |

TABLE 4-continued

Tumor response of patients with KRAS wild type (n = 34) and KRAS mutated (n = 10) metastatic or locally advanced colorectal cancer treated with anti-EGFR therapy according to different cut-off values of EGFR Gene Copy Number and Chromosome 7 number Evaluated by SISH

| | Total No. of patients | PR | SD | PD | p-value Fisher's Exact Test | PFS time median (days) | p-value Log-Rank Test (PFS) | HR | 95% CI | OS time median (days) | p-value Log-Rank Test (OS) | HR | 95% CI |
|---|---|---|---|---|---|---|---|---|---|---|---|---|---|
| EGFR gene copy number | | | | | | | | | | | | | |
| ≥4.0 | 22 | 7 (31.8) | 12 (54.6) | 3 (13.6) | <0.0001 | 236.5 | <0.0001 | 0.11 | 0.04-0.31 | 347 | 0.03 | 0.40 | 0.16-0.91 |
| <4.0 | 12 | 1 (8.3) | 0 | 11 (91.7) | | 75.5 | | | | 118 | | | |
| ≥2.92 | 26 | 7 (26.9) | 12 (46.2) | 7 (26.9) | 0.006 | 213 | <0.0004 | 0.21 | 0.08-0.55 | 320 | <0.0001 | 0.14 | 0.05-0.42 |
| <2.92 | 8 | 1 (12.5) | 0 | 7 (87.5) | | 77.5 | | | | 114 | | | |
| Chromosome 7 number | | | | | | | | | | | | | |
| ≥4.5 | 20 | 7 (35.0) | 10 (50.0) | 3 (15.0) | 0.001 | 227 | 0.004 | 0.33 | 0.15-0.71 | 320 | 0.29 | 0.62 | 0.27-1.43 |
| <4.5 | 14 | 1 (7.1) | 2 (14.3) | 11 (78.6) | | 77 | | | | 134 | | | |
| ≥2.92 | 27 | 7 (25.9) | 12 (44.5) | 8 (29.6) | 0.02 | 203 | 0.001 | 0.23 | 0.09-0.62 | 298 | 0.0004 | 0.18 | 0.06-0.50 |
| <2.92 | 7 | 1 (14.3) | 0 | 6 (85.7) | | 79 | | | | 111 | | | |

Abbreviations: SISH, silver in situ hybridization; EGFR, epidermal growth factor receptor; CR, complete response; PR, partial response; SD, stable disease; PD, progressive disease; PFS, progression free survival; OS, overall survival; WT, wild type; MT, mutated; HR, hazards ratio

The invention claimed is:

1. A method for detecting and analyzing whether a patient suffering from a cancer is responsive or non-responsive to the treatment with an EGFR inhibitor, the method comprising the steps of:
   (a) determining in a tissue section from a tumor sample obtained from said patient
       (i) the expression level of an EGFR protein in said tissue section by immunohistochemistry (IHC), and
       (ii) the level of EGFR gene copy number or the level of copy number of chromosome 7 by enzymatic metallography, wherein an area of highest expression of EGFR in a tissue section from said tumor sample is determined by IHC based on staining intensity, and using enzymatic metallography, a gene copy number of EGFR gene or chromosome 7 is counted from the cells residing in said area of highest expression in the tumor sample; and
   (b) selecting said patient for treatment with said EGFR inhibitor, if the tumor sample of said patient displays expression of EGFR protein and an amplified copy number of the EGFR gene or chromosome 7.

2. The method according to claim 1, wherein the same tissue section from said tumor sample is used in IHC and in enzymatic metallography.

3. The method according to claim 1, wherein consecutive tissue sections from said tumor sample are used in IHC and in enzymatic metallography.

4. The method according to claim 1, wherein the level of EGFR gene copy number or the level of copy number of chromosome 7 is determined as ratio of the number of EGFR genes or chromosome 7 per nucleus.

5. The method according to claim 1, wherein said enzymatic metallography is silver in situ hybridization (SISH) analysis.

6. The method according to claim 1, wherein the patient is selected for the treatment with the EGFR inhibitor, if the level of EGFR gene copy number or the level of copy number of chromosome 7 is statistically similar to or greater than the threshold level of EGFR gene copy number or level of copy number of chromosome 7 that has been correlated with response to the treatment with the EGFR inhibitor.

7. The method according to claim 1, wherein the patient is not selected for the treatment with the EGFR inhibitor, if the level of EGFR gene copy number or the level of copy number of chromosome 7 is statistically less than the threshold level of EGFR gene copy number or level of copy number of chromosome 7 that has been correlated with response to the treatment with the EGFR inhibitor.

8. The method according to claim 4 or 6, wherein the patient is selected for the treatment with the EGFR inhibitor, if the level of EGFR gene copy number is ≥4.0 or the level of copy number of chromosome 7 in nucleus is ≥4.5.

9. The method according to claim 1, wherein said cancer is colorectal cancer, lung cancer, head and neck cancer, or glioma.

10. The method according to claim 1, wherein IHC is performed with an anti-EGFR antibody.

11. The method according to claim 10, wherein said antibody binds to an intracellular domain of the EGFR.

12. The method according to claim 10, wherein said antibody is clone 5B7 or 3C6.

13. The method according to claim 1, wherein said EGFR inhibitor is an antibody or a kinase inhibitor.

14. The method according to claim 13, wherein said antibody is cetuximab (mAb c225), matuzumab (mAb h425) or panitumumab (mAb ABX).

15. The method according to claim 13, wherein said kinase inhibitor is erlotinib or gefitinib.

16. The method according claim 1 further comprising the step of determining the presence or absence of KRAS mutation in said tumor sample.

17. The method according to claim 1 further comprising the step of determining the presence of absence of a mutated EGFR gene or EGFR protein in said tumor sample.

18. The method according claim 1, wherein said tissue section is prepared on a microscope slide.

19. The method according to claim 1, wherein said tissue section is ≤5 μm thick.

20. The method according to claim 1, wherein steps (i) and (ii) are performed with an automated processing apparatus.

21. The method according to claim 1, wherein said enzymatic metallography is silver in situ hybridization (SISH) analysis and wherein said cancer is colorectal cancer.

22. The method according to claim 1, wherein the level of staining is determined based on membraneous, cytoplasmic and/or a combination of cytoplasmic and membraneous staining of the cells in a tumor sample.

23. A method of treating a patient suffering from a cancer comprising the steps of obtaining a tumor sample from said patient, analyzing said sample by the method according to claim 1 and administering an EGFR inhibitor to said patient, if said patient was selected for treatment with said EGFR inhibitor.

* * * * *